(12) United States Patent
Rafiee et al.

(10) Patent No.: US 7,699,892 B2
(45) Date of Patent: Apr. 20, 2010

(54) MINIMALLY INVASIVE PROCEDURE FOR IMPLANTING AN ANNULOPLASTY DEVICE

(75) Inventors: Nasser Rafiee, Andover, MA (US); Nareak Douk, Lowell, MA (US); Eliot Bloom, Hopkinton, NH (US); Michael Finney, Beverly, MA (US); Morgan House, Newfields, NH (US); Rany Huynh, Charlestown, MA (US); Stuart Mac Donald, Haverhill, MA (US); Juan-Pablo Mas, Somerville, MA (US); David Barone, Lexington, MA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 266 days.

(21) Appl. No.: 11/734,604

(22) Filed: Apr. 12, 2007

(65) Prior Publication Data

US 2007/0244557 A1    Oct. 18, 2007

Related U.S. Application Data

(60) Provisional application No. 60/794,553, filed on Apr. 12, 2006, provisional application No. 60/791,340, filed on Apr. 12, 2006, provisional application No. 60/793,879, filed on Apr. 21, 2006.

(51) Int. Cl.
*A61F 2/24* (2006.01)
(52) U.S. Cl. ............ 623/2.37; 623/2.36; 128/898
(58) Field of Classification Search ........... 623/2.36, 623/2.37
See application file for complete search history.

(56) References Cited

U.S. PATENT DOCUMENTS

| | | |
|---|---|---|
| 5,545,148 A | 8/1996 | Wurster |
| 5,582,616 A | 12/1996 | Bolduc et al. |
| 5,682,906 A | 11/1997 | Sterman et al. |
| 5,810,882 A * | 9/1998 | Bolduc et al. ............ 606/213 |
| 5,891,159 A | 4/1999 | Sherman et al. |
| 5,935,138 A | 8/1999 | McJames, II et al. |
| 5,972,020 A | 10/1999 | Carpentier et al. |
| 6,182,664 B1 | 2/2001 | Cosgrove |
| 6,250,308 B1 | 6/2001 | Cox |
| 6,258,069 B1 | 7/2001 | Carpentier et al. |
| 6,514,263 B1 | 2/2003 | Stefanchik et al. |
| 6,524,338 B1 | 2/2003 | Gundry |
| 6,562,051 B1 | 5/2003 | Bolduc et al. |
| 6,619,291 B2 | 9/2003 | Hlavka et al. |
| 6,626,917 B1 | 9/2003 | Craig |
| 6,663,633 B1 | 12/2003 | Pierson, III |
| 6,689,164 B1 | 2/2004 | Sequin |

(Continued)

FOREIGN PATENT DOCUMENTS

WO    WO01/00114    1/2001

(Continued)

*Primary Examiner*—Corrine M. McDermott
*Assistant Examiner*—Rebecca Straszheim

(57) ABSTRACT

A method for modifying a heart valve annulus includes placing a purse string suture at a puncture site adjacent a heart valve, inserting at least one delivery member through the puncture site, positioning a distal end of the at least one delivery member adjacent a portion of a valve annulus, deploying an annuloplasty device carried within the at least one delivery member and implanting the annuloplasty device into the valve annulus. The method also includes reshaping the heart valve annulus after implantation of the at least one annuloplasty device.

5 Claims, 20 Drawing Sheets

U.S. PATENT DOCUMENTS

| | | |
|---|---|---|
| 6,702,826 B2 | 3/2004 | Liddicoat et al. |
| 6,840,246 B2 | 1/2005 | Downing |
| 6,884,248 B2 | 4/2005 | Bolduc et al. |
| 6,902,570 B2 | 6/2005 | Schraft et al. |
| 6,932,792 B1 * | 8/2005 | St. Goar et al. .......... 604/96.01 |
| 6,986,775 B2 * | 1/2006 | Morales et al. ............. 606/139 |
| 7,118,595 B2 | 10/2006 | Ryan et al. |
| 7,175,659 B2 | 2/2007 | Hill et al. |
| 2002/0096183 A1 * | 7/2002 | Stevens et al. .............. 128/898 |
| 2002/0156526 A1 | 10/2002 | Hlavka et al. |
| 2002/0161378 A1 | 10/2002 | Downing |
| 2003/0220685 A1 | 11/2003 | Hlavka et al. |
| 2004/0003819 A1 * | 1/2004 | St. Goar et al. ............. 128/898 |
| 2004/0024414 A1 | 2/2004 | Downing |
| 2004/0049211 A1 * | 3/2004 | Tremulis et al. ............ 606/153 |
| 2004/0236419 A1 | 11/2004 | Milo |
| 2005/0049698 A1 | 3/2005 | Bolling et al. |
| 2005/0065601 A1 | 3/2005 | Lee et al. |
| 2005/0131533 A1 | 6/2005 | Alfieri et al. |
| 2005/0171601 A1 | 8/2005 | Cosgrove et al. |
| 2007/0027533 A1 | 2/2007 | Douk |
| 2007/0051377 A1 | 3/2007 | Douk et al. |
| 2007/0083259 A1 | 4/2007 | Bloom et al. |

FOREIGN PATENT DOCUMENTS

| | | |
|---|---|---|
| WO | WO02/062263 | 8/2002 |
| WO | WO2004/112585 | 12/2004 |
| WO | WO2005/025644 | 3/2005 |
| WO | WO2005/046488 | 5/2005 |
| WO | WO2005/058206 | 6/2005 |

* cited by examiner

MINIMALLY INVASIVE PROCEDURE FOR IMPLANTING AN ANNULOPLASTY DEVICE

CROSS-REFERENCE TO RELATED APPLICATION

The present application claims priority to U.S. Provisional Application 60/791,553, filed Apr. 12, 2006 and titled "Annuloplasty Device Having Helical anchors"; U.S. Provisional Application No. 60/791,340, filed Apr. 12, 2006 and titled "Minimally Invasive Procedure for Implanting an Annuloplasty Device"; and U.S. Provisional Application 60/793,879, filed Apr. 21, 2006 and titled "Annuloplasty Device Having Helical anchors", of which the entire contents of each are incorporated herein by reference.

FIELD OF INVENTION

This invention relates generally to the treatment of heart valves and particularly to systems, devices and methods for treating valvular regurgitation by increasing leaflet coaption.

BACKGROUND

The heart is a four-chambered pump that moves blood efficiently through the vascular system. Blood enters the heart through the vena cava and flows into the right atrium. From the right atrium, blood flows through the tricuspid valve and into the right ventricle, which then contracts and forces blood through the pulmonic valve and into the lungs. Oxygenated blood returns from the lungs and enters the heart through the left atrium and passes through the mitral valve into the left ventricle. The left ventricle contracts and pumps blood through the aortic valve into the aorta and to the vascular system.

The mitral valve consists of two leaflets (anterior and posterior) attached to a fibrous ring or annulus. In a healthy heart, the mitral valve leaflets close during contraction of the left ventricle and prevent blood from flowing back into the left atrium. Due to various cardiac diseases, however, the mitral valve annulus may become distended causing the leaflets to remain partially open during ventricular contraction and thus allow regurgitation of blood into the left atrium. This results in reduced ejection volume from the left ventricle, causing the left ventricle to compensate with a larger stroke volume. However, the increased workload eventually results in dilation and hypertrophy of the left ventricle, further enlarging and distorting the shape of the mitral valve. If left untreated, the condition may result in cardiac insufficiency, ventricular failure, and ultimately death.

It is common medical practice to treat mitral valve regurgitation by either valve replacement or repair. Mitral valve repair includes a variety of procedures to repair or reshape the leaflets to improve closure of the valve during ventricular contraction. If the mitral valve annulus has become distended, a frequent repair procedure involves implanting an annuloplasty ring on the mitral valve annulus. The annuloplasty ring generally has a smaller diameter than the annulus, and when sutured to the annulus the annuloplasty ring draws the annulus into a smaller configuration, bringing the mitral valve leaflets closer together, and allowing improved closure during ventricular contraction. Annuloplasty rings may be rigid, flexible or a combination, having both rigid and flexible segments. Rigid annuloplasty rings have the disadvantage of causing the mitral valve annulus to be rigid and unable to flex in response to the contractions of the ventricle, thus inhibiting the normal, three-dimensional movement of the mitral valve that is required for it to function optimally. Flexible annuloplasty rings are frequently made of Dacron® fabric and must be sewn to the annular ring with a line of sutures. This eventually leads to scar tissue formation and loss of flexibility and function of the mitral valve. Similarly, combination rings must generally be sutured in place and also cause scar tissue formation and loss of mitral valve flexibility and function.

Valve replacement involves an open-heart surgical procedure in which the patient's mitral valve is removed and replaced with an artificial valve. One drawback to open heart surgical techniques requires heart bypass procedures to accomplish the replacement and/or repair of the valve. Another drawback is that the open-heart procedures require that the patient undergo general anesthesia for a prolonged periods of time.

To overcome many of the complications and risks of open-heart surgical procedures, less invasive or minimally invasive surgical techniques have been developed. These procedures can be done on a beating heart and often are performed without general anesthesia or a reduced time under general anesthesia.

It would be desirable, therefore to provide a method and device for reducing valvular regurgitation that would overcome the limitations and disadvantages inherent in the devices described above.

BRIEF SUMMARY OF THE INVENTION

One aspect of the invention provides a method for modifying a heart valve annulus. The method comprises placing a purse string suture at a puncture site adjacent a heart valve, inserting at least one delivery member through the puncture site, positioning a distal end of the at least one delivery member adjacent a portion of a valve annulus, deploying an annuloplasty device carried within the at least one delivery member and implanting the annuloplasty device into the valve annulus.

Another aspect of the invention provides a method modifying a heart valve annulus. The method comprises placing a purse string suture at a puncture site adjacent a heart valve, inserting a first delivery member through the puncture site, positioning a distal end of the first delivery member adjacent a first portion of a valve annulus, deploying a first annuloplasty device carried within the first delivery member, implanting the first annuloplasty device into the first portion of the valve annulus and removing the first delivery member. The method further includes inserting a second delivery member through the puncture site positioning a distal end of the second delivery member adjacent a second portion of a valve annulus, deploying a second annuloplasty device carried within the second delivery member, implanting the second annuloplasty device into the second portion of the valve annulus removing the second delivery member and reshaping the valve annulus.

The present invention is illustrated by the accompanying drawings of various embodiments and the detailed description given below. The drawings should not be taken to limit the invention to the specific embodiments, but are for explanation and understanding. The detailed description and drawings are merely illustrative of the invention rather than limiting, the scope of the invention being defined by the appended claims and equivalents thereof. The drawings are not to scale. The foregoing aspects and other attendant advantages of the present invention will become more readily appreciated by the detailed description taken in conjunction with the accompanying drawings.

DETAILED DESCRIPTION

The invention will now be described by reference to the figures wherein like numbers refer to like structures. The terms "distal" and "proximal" are used herein with reference to the treating clinician during the use of the system; "Distal" indicates an apparatus portion distant from, or a direction away from the clinician and "proximal" indicates an apparatus portion near to, or a direction towards the clinician. Additionally, the term "annuloplasty" is used herein to mean modification/reconstruction of a defective heart valve.

The current invention discloses systems, devices, and methods for treating regurgitation in cardiac valves. While these systems, devices, and methods are described below in terms of being used to treat mitral regurgitation, it will be apparent to those skilled in the art that the devices could be used on other cardiac valves also. Annuloplasty devices of the current invention comprise helical anchors, tethers, and locks and they are used to modify the shape of heart valves for treating valvular regurgitation. The systems of the current invention comprised the annuloplasty devices and the delivery members for placing the devices adjacent a heart valve annulus. The annuloplasty devices of the current invention are delivered to, and implanted in, a beating heart using a minimally invasive surgical technique.

Figure 1:
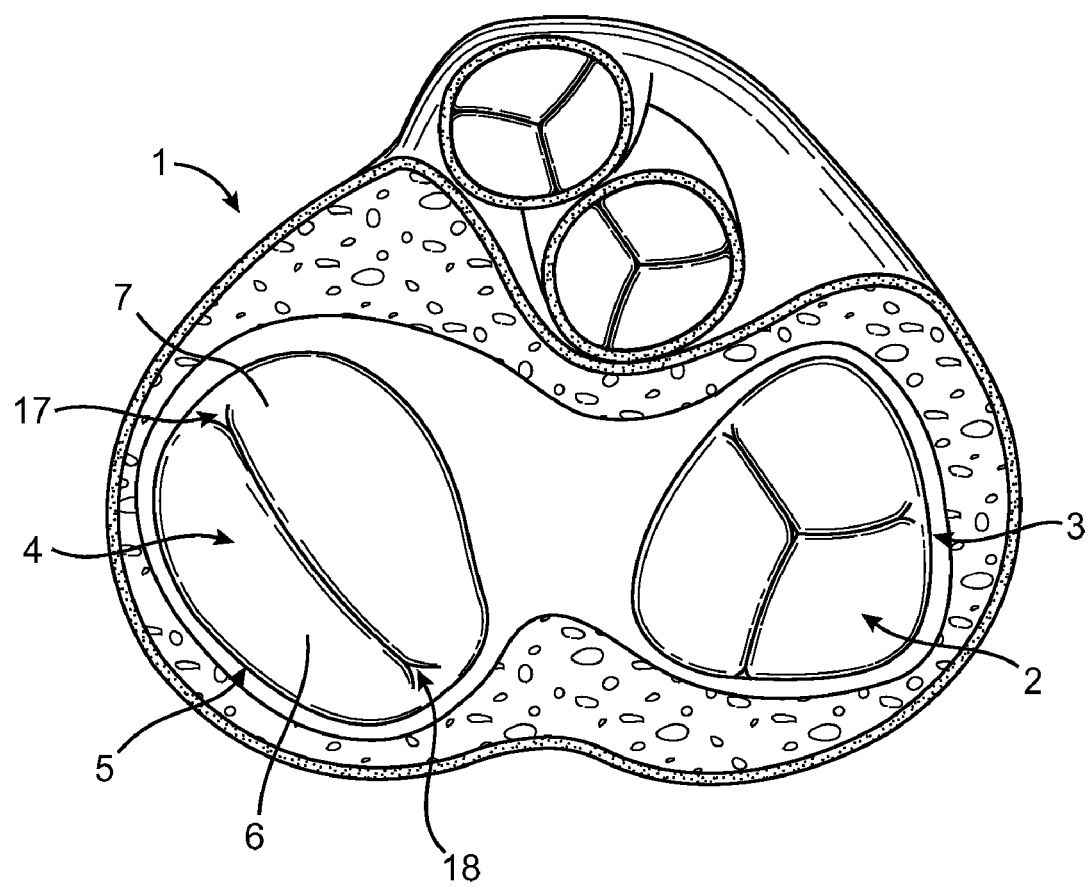
FIG. 1 is a cross-sectional schematic view of a heart showing the location of the heart valves.

Referring to the drawings, FIG. 1 shows a schematic cross-sectional view of a heart 1 having tricuspid valve 2 and tricuspid valve annulus 3. Mitral valve 4 is adjacent mitral valve annulus 5. Mitral valve 4 is a bicuspid valve having anterior cusp 7 and posterior cusp 6. Anterior cusp 7 and posterior cusp 6 are often referred to, respectively, as the anterior and posterior leaflets. Also shown in the figure are the posterior commisure 17 and the anterior commisure 18.

Figure 2A:
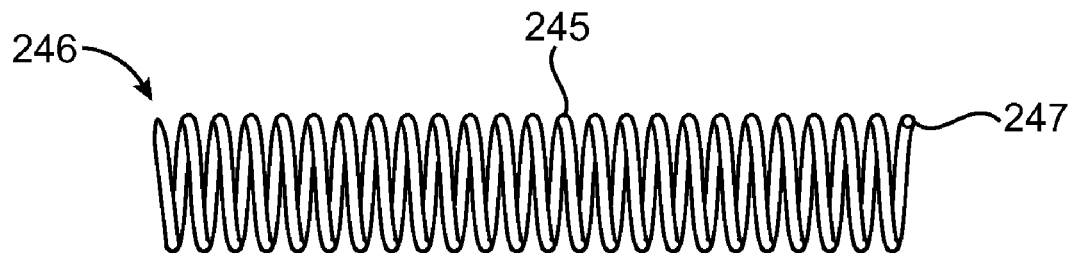
FIGS. 2A and 2B illustrate a helical anchor for an annuloplasty device according to the current invention.
Figure 2B:
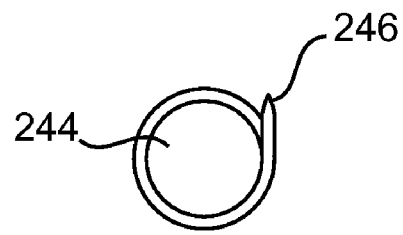

Referring first to FIGS. 2A and 2B, there is shown a helical anchor for an annuloplasty device according to the current invention. Helical anchor 245 comprises an elongate coiled member having a tissue penetrating tip 246 at a distal end and a proximal end 247 that is operably connected to a helical anchor driver.

Helical anchor 245 comprises a biocompatible metallic or polymeric material having suitable resiliency. In one embodiment, helical anchor 245 comprises stainless steel, in another embodiment, the helical anchor comprises 35NLT, and in yet another embodiment the helical anchor comprises MP35N. The diameter of the metallic or polymeric member that is coiled to make the helical anchor can vary based on the desired flexibility, the size of the annulus, the delivery method, etc, and some embodiments include helical anchors made from wires with diameters in a range of 0.017 inches to 0.025 inches One embodiment is made from a material with a diameter smaller than 0.017 inches, another embodiment is made from a material with a diameter larger than 0.025 in, and yet another embodiment is made from a material having a diameter of 0.02 inches The coils of the helical anchor define an inner channel for a tether. Thus, the helical anchor has an outer diameter defining the exterior of the helical anchor and an inner diameter defining the channel or lumen through the helical anchor. Some embodiments of the invention include helical anchors having inner channel diameters in the range of 0.10 inches to 0.20 inches One embodiment includes a helical anchor with an inner channel diameter smaller than 0.10 inches, another embodiment has a helical anchor with an inner channel diameter larger than 0.20 inches, and yet another embodiment has a helical anchor with an inner channel diameter of 0.11 inches Outer diameters for the helical anchors are in the range of 0.150 inches to 0.250 inches One embodiment includes a helical anchor with an outer diameter smaller than 0.150 inches, another embodiment has a helical anchor with an inner diameter larger than 0.250 inches, and yet another embodiment has a helical anchor with an outer diameter of 0.150 inches.

The coils of the helical anchor define an inner channel for a tether. Thus, the helical anchor has an outer diameter defining the exterior of the helical anchor and an inner diameter defining the channel or lumen through the helical anchor. Some embodiments of the invention include helical anchors having inner channel diameters in the range of 0.10 inches to 0.20 inches. One embodiment includes a helical anchor with an inner channel diameter smaller than 0.10 inches, another embodiment has a helical anchor with an inner channel diameter larger than 0.200 inches, and yet another embodiment has a helical anchor with an inner channel diameter of 0.11 inches. Outer diameters for the helical anchors are in the range of 0.150 inches to 0.250 inches. One embodiment includes a helical anchor with an outer diameter smaller than 0.150 inches, another embodiment has a helical anchor with an inner diameter larger than 0.250 inches, and yet another embodiment has a helical anchor with an outer diameter of 0.150 inches.

The distance between each coil defines the coil pitch, and the pitch can also be expressed as the number of coils per inch. The number of coils per inch for the helical anchors of the current invention can vary based on the desired degree of flexibility and resiliency. Some embodiments include helical anchors having coils per inch in the range of 10 to 20. One embodiment of a helical anchor has less than 10 coils per inch, one embodiment of a helical anchor has more than 20 coils per inch, and one embodiment of a helical anchor according to the current invention has 12 coils per inch. An additional embodiment of the current invention includes helical anchors having 14 coils per inch.

In addition to the pitch, the length of the helical anchors of the various embodiments of the invention can vary based on the size of a patient's valve annulus and the number and location of helical anchors needed to modify the shape of the annulus. In one embodiment of the invention, multiple helical anchors having six coils each are implanted. In another embodiment, a single helical anchor that is 1 inch long is implanted. Some embodiments of the invention include helical anchors having a length in the range of 0.50 inches to 2.5 inches. At least one embodiment has at least one helical anchor longer than 2.5 inches and another embodiment has at least one helical anchor shorter than 0.50 inches. In at least one embodiment of the invention, helical anchors having a length in the range of 25 mm to 31 mm are implanted in the anterior portion of a mitral valve annulus. In at least one embodiment of the invention, helical anchors having a length in the range of 59 mm to 63 mm are implanted in the posterior portion of a mitral valve annulus. In another embodiment of the invention, a plurality of helical anchors having lengths in the range of 0.40 to 2.50 inches are used to alter the shape of a valve annulus. One embodiment of the invention uses a plurality of helical anchors having the same length to modify the shape of a heart valve annulus. Another embodiment of the invention uses a plurality of helical anchors where not all of the helical anchors have the same length, but some of the helical anchors have the same length.

The flexibility of the helical anchor can be controlled by the diameter of the wire or other material used to make the helical anchor and the number of coils per inch. As will be described further below a tether will be placed through the inner channel of one or more helical anchors that are implanted along a heart valve annulus. The tether will then be manipulated to exert a force on the helical anchors and modify the shape of the valve annulus. Care must be taken when choosing a helical anchor to insure that the helical anchor will be able to maintain a modified position after it has been implanted. If a helical anchor is made from a wire or other member having too large of a diameter or if a helical anchor is made with too many coils per inch, more pressure will be required to keep the helical anchor from moving to a straight elongated state. In at least one embodiment, at least a portion of the helical anchor is made from material having a high X-ray attenuation coefficient.

Helical anchor 245 comprises a plurality of individual coils. The plurality of coils form a generally cylindrical inner channel 244 that can accommodate an anchor guide and through which a portion of a tether will be disposed. In operation, the inner channel diameter, the coil pitch and the length of the tip 246 of the helical anchor may be determined to provide a specific depth of penetration of the helical anchor 245 as it is threaded along the valve annulus.

In one embodiment (not shown), a system will include a tip sheath that can be disposed on the tip of a helical anchor. The tip sheath encases the helical anchor tip when the helical anchor is in a deployed configuration. In one embodiment, a helical anchor tip sheath includes an opening through which a tether passes.

Figure 3A:
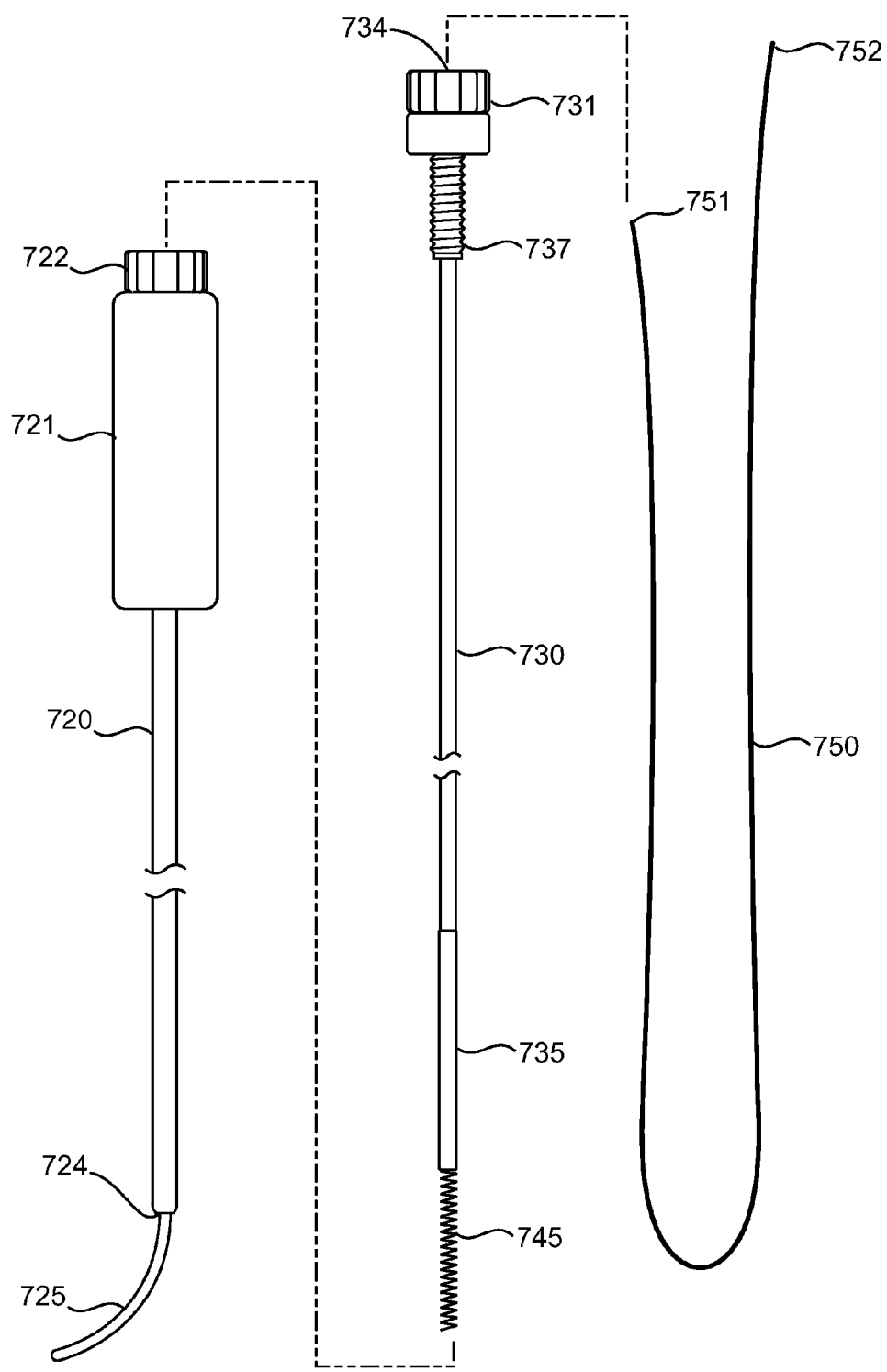
FIGS. 3A-3C illustrate a system for modifying the shape of a heart valve annulus according to the current invention.
Figure 3B:
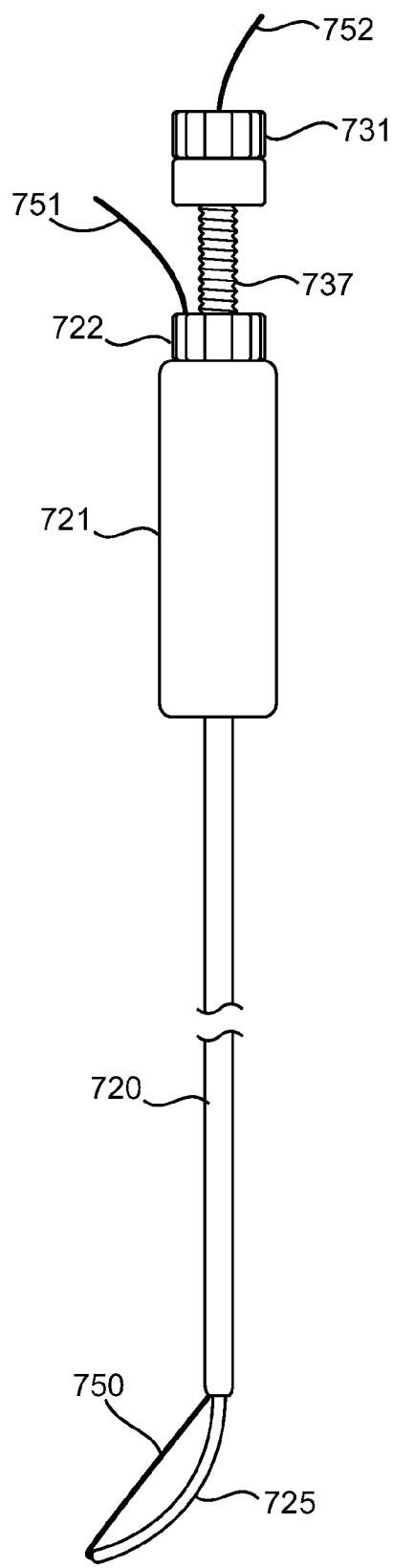
Figure 3C:
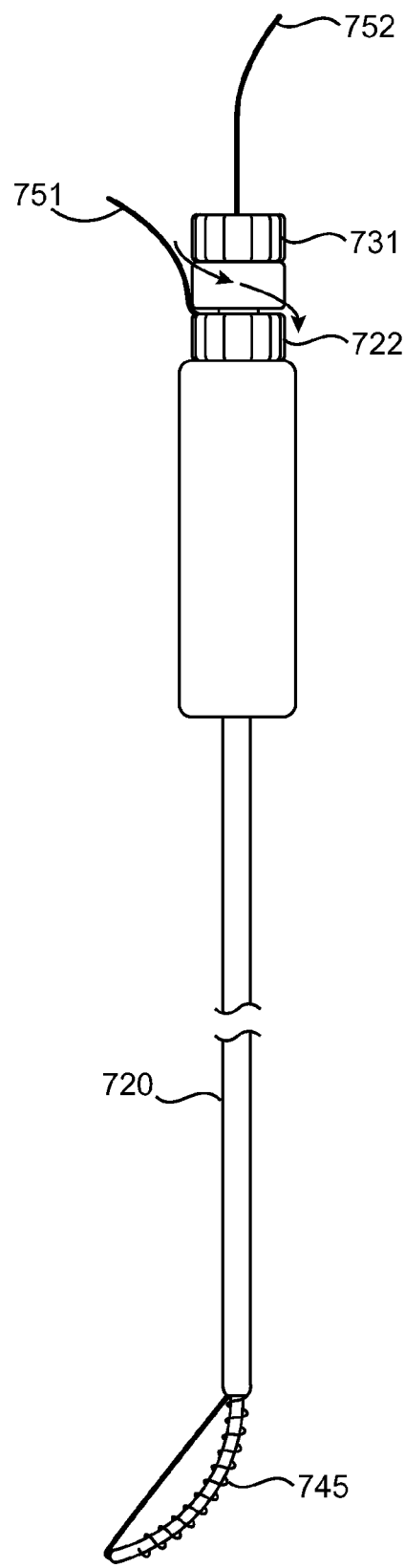

Referring now to FIGS. 3A through 3C, there is shown an embodiment of a system used for a valve modification procedure where access is gained to a heart valve via a minimally invasive surgical approach and the procedure can be done on a beating heart.

FIG. 3A shows the elongated generally tubular delivery member 720 having a handle 721 and a handle cap 722 on the proximal end of the delivery member 720. The distal end of the delivery member 720 includes an anchor guide 725 and the distal opening 724 of the driver lumen that communicates through the length of the delivery member.

The anchor guide 725 is can be configured to conform to the shape of at least a portion of the valve annulus when the anchor guide is placed next to a valve annulus at the treatment site. In one embodiment of the invention, the anchor guide is configured to conform to the annulus adjacent the posterior leaflet of a mitral valve. In another embodiment of the invention, the anchor guide is configured to conform to the annulus adjacent the anterior leaflet of a mitral valve.

An elongated helical anchor driver 730 includes a driver knob 731 on the proximal end of the driver and a threaded portion 737 adjacent the knob. A distal portion 735 of the driver is connected to a helical anchor 745. The driver can be made from any biocompatible material sufficient to allow the driver to rotate and to move longitudinally inside of the delivery member, and translate the rotation and movement to the helical anchor. Most of the driver shaft can be stiff, but the distal portion 735 must be flexible to allow the driver to negotiate any curved portions near the distal end of the delivery member 720.

Figure 4:
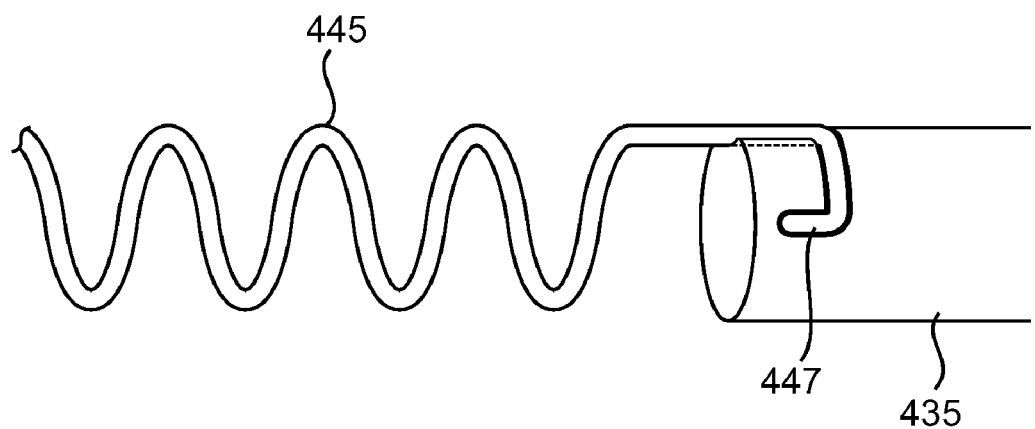
FIGS. 4 and 5 illustrate the attachment of helical anchors to an helical anchor driver according to the current invention.
Figure 5:
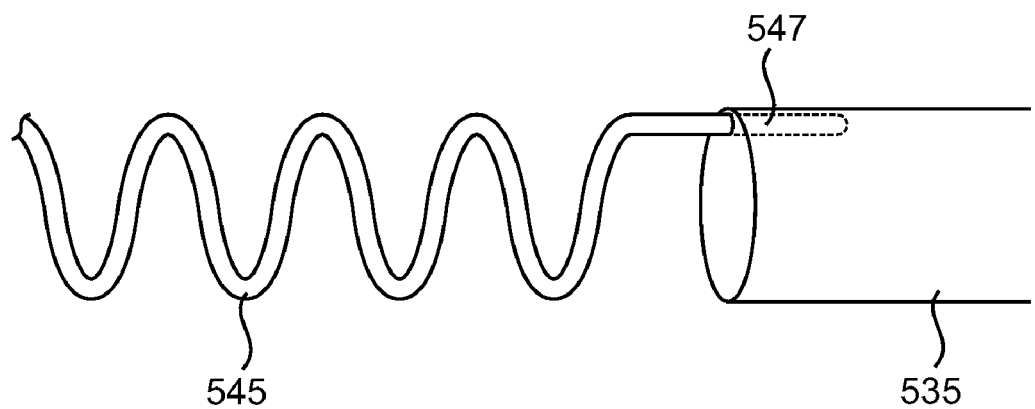

Referring to FIGS. 4 and 5, there can be seen two different embodiments of how the helical anchors of the current invention can be connected to the proximal end of the helical anchors of the current invention. FIG. 4 shows a helical anchor 445 according to the current invention wherein the helical anchor has a generally U-shaped driver portion 447 at the proximal end. The distal end 435 of the driver has an indentation in the driver's outer surface that is sized and shaped so that the driver portion at the proximal end of the helical anchor will fit snugly into the driver during delivery of the helical anchor. Once the helical anchor is implanted in a valve annulus, the driver is rotated in the opposite direction than the rotation for implanting the valve and the delivery member is manipulated so that the helical anchor separates from the driver.

FIG. 5 illustrates another embodiment of a release mechanism according to the current invention. The helical anchor 545 has a proximal end 547 with a driver portion that extends straight in a proximal direction from the helical anchor. The distal tip 535 of the driver has a hole for placement of the driver portion of the helical anchor such that the helical anchor will fit snugly into the driver during implantation. Once the helical anchor is implanted, the driver and delivery member are pulled away from the proximal end of the helical anchor and the straight driver portion of the proximal end is pulled from the hole in the distal tip of the driver. In some embodiments of the current invention, the length of the straight driver portion of the helical anchor can vary from 0.05 inches to 0.25 inches. Some embodiments of the current invention have helical anchors with straight driver portions that are longer than 0.25 inches, other embodiments of the current invention have helical anchors with straight driver portions that are shorter than 0.05 inches, and one embodiment of a helical anchor according to the current invention has a helical anchor with a straight driver portion of 0.10 inches.

In some embodiments of the current invention, the driver can be a hollow member having either a tether lumen or an anchor guide lumen communicating through its length. The helical anchor connections shown in FIGS. 4 and 5 will work equally as well for tubular driver members as they will for non-tubular driver members.

Referring again to FIG. 3A, the system also includes a flexible elongated tether 350 having a first end 351 and a second end 352. Tether 350 comprises an elongate flexible filament of biocompatible material. In one embodiment, the tether comprises a monofilament. In other embodiments the tether may comprise a braid of a plurality of filaments of the same material or of filaments from different materials. Still other embodiments of tethers comprise a braded sheath with a single filament core, or a braided sheath with a braided core. The tether 350 may be composed of biocompatible material such as, but not limited to, nylon or polyester. The tether may be constructed from material that will not stretch or it may be pre-stressed to prevent the tether from elongating after the annuloplasty devices of the current invention are implanted in a heart valve annulus. In one embodiment, the tether is made from a pre-stretched ultra-high-molecular-weight polyethylene. Various embodiments of the invention include tethers having diameters in the range of 0.015 inches and 0.050 inches in diameter.

The tether 750 is delivered to the treatment site in a looped configuration with first and second ends extending outside the patient's body during the implantation procedure. If additional helical anchors are desired, the ends of the tether are threaded through an additional driver, helical anchor and delivery member based on where the preceding helical anchor was implanted and where the new helical anchor will be planted relative to the preceding helical anchor.

To use the system, the first end 751 of the tether 750 is threaded into a tether lumen 734 at the proximal end of the driver and out through an inner channel of the helical anchor 745. The tether is then threaded into the driver lumen and into a tether lumen (not shown) in the anchor guide 725. The tether exits the end of the anchor guide and is routed back up through the driver lumen and exits the handle 721 through another tether lumen (not shown).

Referring to FIG. 3B, the driver 730 is inserted into the driver lumen of the delivery member 720 and advanced until the threaded portion 737 makes contact with a complementary threaded portion (not shown) on the interior of the delivery member handle 721. When the driver has been advanced to the point where the threaded portion on the driver makes contact with the threaded portion on the handle, the helical anchor 745 will be located adjacent to the anchor guide. The anchor guide 725 would then be aligned with a valve annulus and placed on the annulus in the desire location for implanting the helical anchor. Also shown in FIG. 3B are the first end 751 and the second end 752 of the tether 750; the handle cap 722 and the helical anchor 745.

Referring now to FIG. 3C, the driver knob 731 is rotated so that the threaded portion 737 on the driver is screwed into the complementary threaded portion of the delivery member 720. As the driver is threaded into the delivery member, the distal portion of the driver rotates and moves toward the distal opening 724 of the delivery member until the distal end of the helical anchor is extended from the delivery member and the distal end is rotated into and out of the valve annulus while the helical anchor is rotated along the anchor guide. Also shown in FIG. 3C are the first end 751 and the second end 752 of the tether 750; the handle 721 with handle cap 722 and the anchor guide 725. FIG. 3C further depicts driver 730.

In some embodiments of the systems of the current invention, the helical anchor is engaged to the distal tip of the driver and the driver and helical anchor are placed in the delivery member such that the anchor guide is already in the inner channel of the helical anchor. In other embodiments, the extended distal tip of the helical anchor catches the anchor guide, as the distal end of the helical anchor extends from the distal opening of the delivery member, and the helical anchor rotates itself onto and along the delivery guide as the driver is threaded into the delivery member.

Once the helical anchor is implanted, the anchor guide is either withdrawn into the delivery member or the delivery member is rotated and manipulated to remove the anchor guide from the inner channel of the helical anchor. After the anchor guide is removed from the helical anchor, a portion of the tether remains disposed in the helical anchor such that one end of the tether extends from the distal end of the helical anchor and the other end of the tether extends from the proximal end of the helical anchor.

The delivery member and driver are then withdrawn from the area of the valve annulus. The tether slides freely through the tether lumens or other portions of the delivery member and driver while they are being withdrawn, and it can be completely removed from those portions of the system such that the ends extend outside of a patient's body while a portion of the tether is disposed in the inner channel of the helical anchor implanted in the patient's heart valve annulus.

In some embodiments of the invention where additional helical anchors are desired, the delivery member and driver are withdrawn and additional delivery members and drivers are selected. The tether is threaded into tether channels or other appropriate structure of the delivery members, drivers, and helical anchors such that the helical anchors can be implanted. The tether is threaded through the additional drivers, helical anchors, and delivery members based on where the preceding helical anchor was implanted and where the new helical anchor will be planted relative to the preceding helical anchor.

In at least one embodiment where multiple helical anchors are desired, the delivery member is left inside of a patient's body and the driver is withdrawn from the delivery member. The tether is threaded into an additional helical anchor and driver. The driver is then inserted into the delivery member and advanced so that the helical anchor is at the distal opening in the delivery member. The anchor guide is then manipulated so that it is placed on the portion of the valve annulus where the additional helical anchor is desired, and the helical anchor is implanted as described above. Other additional helical anchors can be implanted using the same delivery member, or the delivery member can be withdrawn and other additional helical anchors implanted using additional delivery members and drivers as described above.

Once a desired number of helical anchors have been implanted, the clinician forms a loop out of the tether and makes the loop smaller to apply a force to the helical anchors and modify the shape of the valve annulus. When the shape of the valve annulus has reached a desired level of modification, the tether is secured (as described below) so that the valve annulus will be maintained in the desired state of modification. Any excess material on the tether is then trimmed away.

The components of the system depicted in FIGS. 3A through 3C can be made from any suitable biocompatible material. The delivery member 720 can be made of flexible, biocompatible polymeric material such as, but not limited to, polyurethane, polyethylene, nylon and polytetrafluoroethylene (PTFE), it can be made from rigid plastics or metals such as stainless steel or other suitable metals, and it can be made from a combination of two or more of these materials.

The driver 730 can also be made from flexible, biocompatible polymeric material such as, but not limited to, polyurethane, polyethylene, nylon and polytetrafluoroethylene (PTFE). Portions of the driver can be made from rigid plastics or metals such as stainless steel of other suitable metals as long as the distal portion of the driver is made from a flexible material that will allow it to negotiated curved portions of the delivery member. In one embodiment, the proximal portion of the driver is a braided member formed from a plurality of metallic filaments. In other embodiments, the drivers can include portions made from polymeric filaments or a combination of metallic and polymeric filaments. In some embodiments of the invention, the braided portions of drivers are braided sheaths having lumens for tethers and anchor guides running therethrough.

The lumens of the delivery members and drives of the current invention can be coated with a lubricious material such as silicone, polytetrafluroethylene (PTFE), or a hydrophilic coating. The lubricious interior surface of a delivery member facilitates the longitudinal movement of a driver The anchor guide 725 can be made from a suitable biocompatible metallic or polymeric material or combinations thereof. The anchor guides of the current invention can be made from a flexible material, but the material must be hare enough to resist penetration by the sharpened distal end of a helical anchor. In one embodiment of the invention, the anchor guide is made from stainless steel. In one embodiment of the invention, the tubular delivery member and the anchor guide are formed as a unitary piece from a biocompatible material. In other embodiments, the delivery members and anchor guides are fashioned as separate pieces that are joined together by, for example, adhesive, welding or any other manner known in the art. In another embodiment of the invention, the delivery member comprises a polymeric material and the anchor guide comprises a metal.

The anchor guide can have a generally circular or elliptical cross-section such that at least a portion of the exterior surface of the guide has a shape that is complementary to the radius of curvature of helical anchor. During deployment of helical anchor, the helical anchor contacts surface of the anchor guide, which guides the helical anchor as it advances along the length of anchor guide.

During the delivery of a helical anchor to a valve annulus, the various components of the system are concentrically disposed within the delivery member. Those with skill in the art will recognize that the arrangement of the various components within the delivery member may be different from that described and illustrated in the figures.

Figure 6:
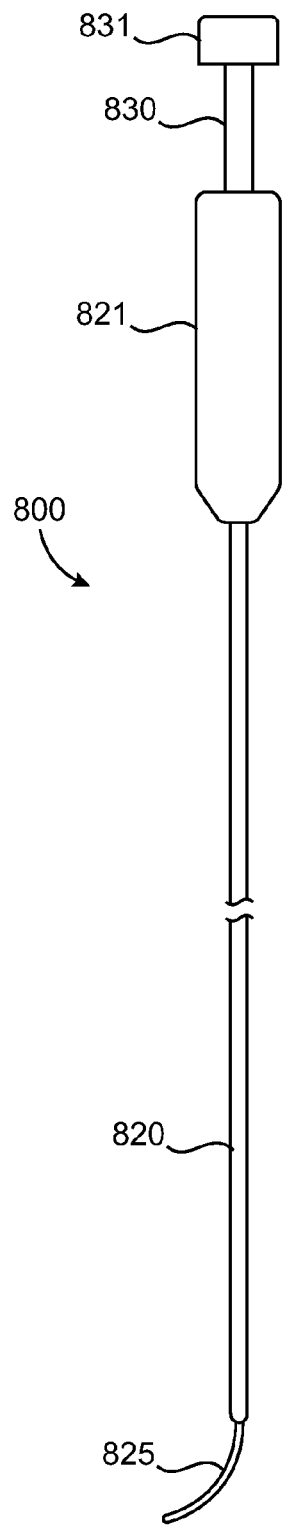
FIGS. 6 and 7 illustrate embodiments of delivery members that are used in annulus modification systems according to the current invention.
Figure 7:
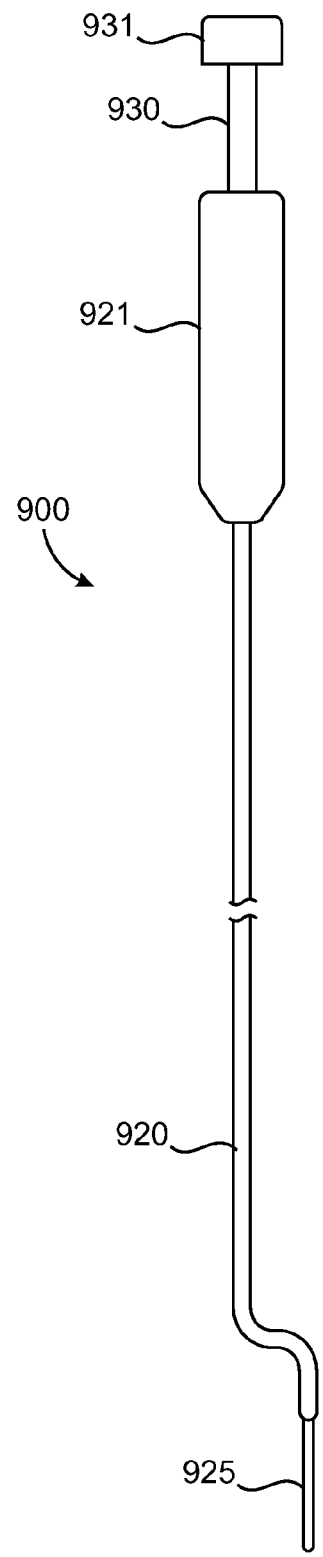

FIGS. 6 and 7 illustrate other embodiments of annulus modification systems in accordance with the present invention. The systems depicted in the figures can be used for implanting helical anchors using a minimally invasive surgical procedure. The systems include many of the same components as those systems described above and thus will not be described in great detail. Referring to FIG. 6, system 800 comprises a system having an elongated tubular helical anchor 820 with an anchor guide 825 on the distal end thereof. A handle 821 is located on the proximal end of the delivery member. A driver 830 is disposed in a helical anchor lumen (not shown). A driver knob 831 is disposed on the proximal end of the driver, and a helical anchor (not shown) is disposed on the distal end. A tether (not shown) is disposed within the driver and delivery member. The anchor guide has a curved shaped to correspond with the shape of a portion of the heart valve. The system includes other components similar to those described above and it works the same way as those described above.

Referring now to FIG. 7, system 900 comprises a system having an elongated tubular helical anchor 920 with an anchor guide 925 on the distal end thereof. A handle 921 is located on the proximal end of the delivery member. A driver 930 is disposed in a helical anchor lumen (not shown). A driver knob 931 is disposed on the proximal end of the driver, and a helical anchor (not shown) is disposed on the distal end. A tether (not shown) is disposed within the driver and delivery member. The anchor guide of the depicted embodiment has a relatively straight shape for use in implanting helical anchors along relatively straight portions of a valve annulus. The system includes other components similar to those described above and it works the same way as those described above.

Figure 8:
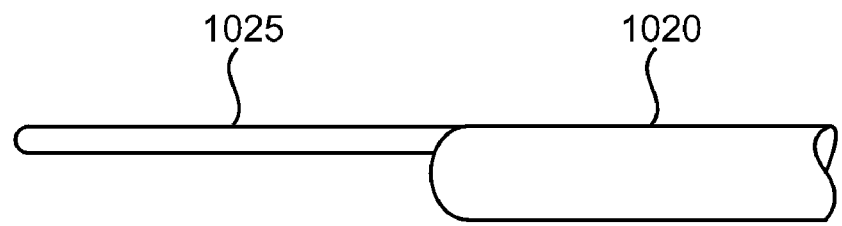
FIGS. 8-15 illustrate a variety of shapes for anchor guides in annulus modification systems according to the current invention.
Figure 9:
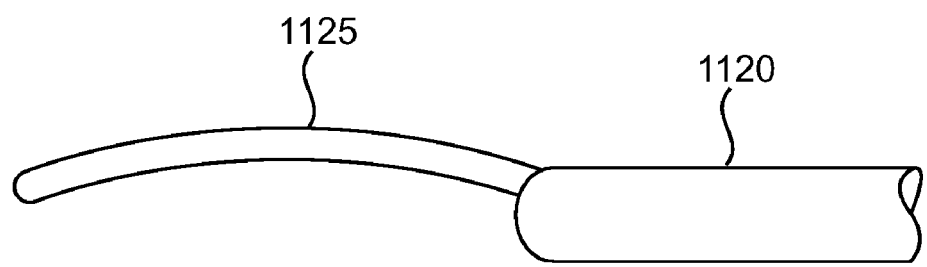
Figure 10:
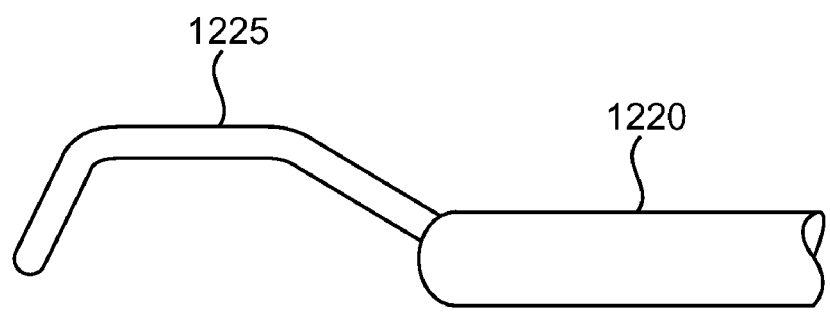
Figure 11:
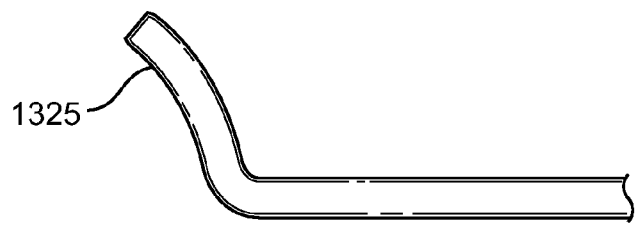
Figure 12:
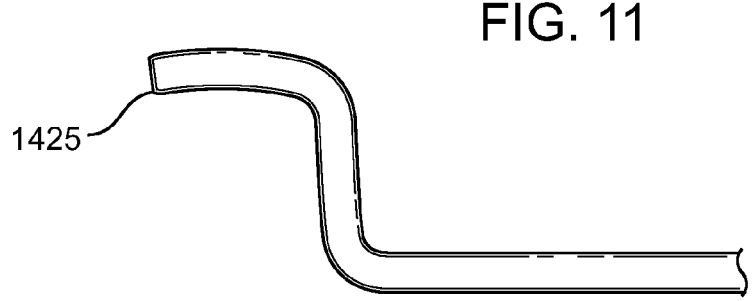
Figure 13:
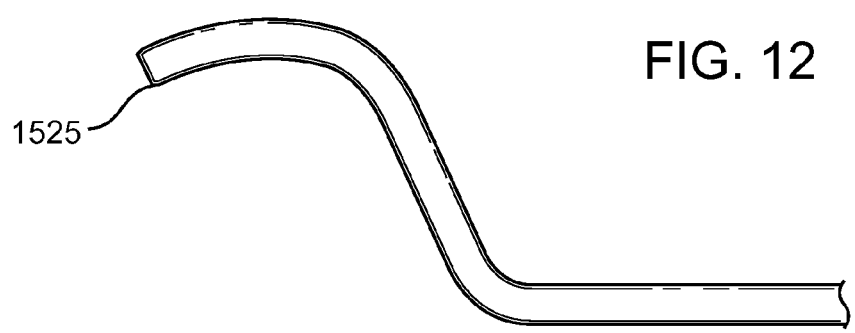
Figure 14:
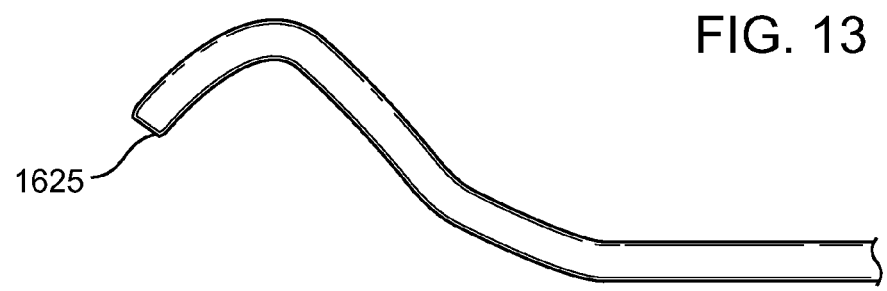
Figure 15:
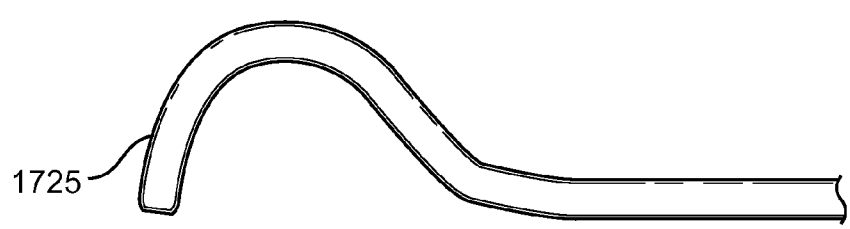

FIGS. 8 through 15 illustrate the variety of shapes that the anchor guides of the current invention can have. FIG. 8 shows the distal end of a delivery member 1020 having a generally linear anchor guide 1025. The linear anchor guide can be used for implanting helical anchors in a location where a valve annulus is relatively straight. FIG. 9 shows the distal end of a delivery member 1120 having a large radius curve anchor guide 1125 that is suited for implanting helical anchors where a valve annulus has a gentle/large radius curvature. FIG. 10 depicts the distal end of a delivery member 1220 having an anchor guide with a plurality of straight sections along its length. The anchor guide depicted in FIG. 10 is suited for a valve annulus that has a very tight curve radius at a location where a helical anchor is desired. In another embodiment (not depicted) the anchor guide can have a plurality of curved sections having different radii for implanting a helical anchor on a section of a valve annulus where the radius of curvature changes along the annulus. FIGS. 11 through 15 illustrate a plurality of anchor guides 1325, 1425, 1525, 1625, and 1725 having a variety of shapes. A clinician can choose delivery members for implanting helical anchors based on the size of the valve annulus, the shape of the valve annulus, the shape of the delivery member relative to the shape valve annulus, and the length of the helical anchor to be implanted.

Various embodiments of the current invention include annuloplasty devices comprising a single helical anchor and a tether or a plurality of helical anchors and a tether. After the helical anchors of the various embodiments are implanted in a heart valve annulus, the tether is manipulated to apply a force to the helical anchors and modify the shape of the heart valve annulus. In some cases, the tether is formed into a loop and the loop is made progressively smaller until a desired degree of modification has been achieved at which time either a knot or other locking device is placed on the tether to secure the loop and maintain the desired state of annulus modification.

In other cases a bead or other device that is too big to pass through the inner channel of a helical anchor is secured to one end of the tether and tension is applied to the other end of the tether to pull the bead against one end of a helical anchor. The application of tension is continued until the shape of the valve annulus has reached a desired state of modification and the tether is secured using another locking device on the other end of the helical anchor or group of helical anchors.

Figure 16A:
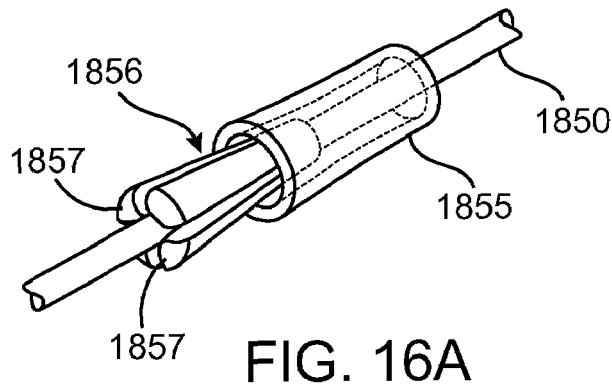
FIGS. 16A, 16B, and 17 illustrate embodiments of locking devices used for annuloplasty devices according to the current invention.
Figure 16B:
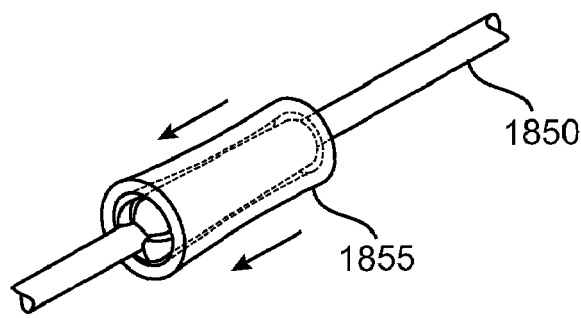

Referring now to FIGS. 16A and 16B, there can be seen a locking device according to the current invention. The locking device comprises a stop member 1855 having a size and shape that will prevent the stop member from entering the inner channel of a helical anchor. In some embodiments of the invention, the stop 1855 will be smaller than the outer diameter of a helical anchor but larger than the diameter of the inner channel. This will allow the stop member to be delivered through a delivery member.

The stop member has at least one lumen communicating through the stop member. A plurality of locking members 1856 can be spaced along the portion of the tether 1850 that will be inside of the helical anchors. The locking members 1856 have a proximal end and a distal end with a plurality of integral legs 1857 that extend at an angle from the locking member. The locking members are made from material having suitable flexibility to allow the legs to compress radially inward when pulled or otherwise moved through the stop member proximal end first, and then recoil radially outward so that they will not pass distally through the stop member. FIG. 16B shows that as the stop member is pushed distally (in the direction of the arrows) along the tether 1850, it is pushed over the locking member. Once the stop member has passed the locking member, it cannot move proximally along the tether unless the legs of the locking member are compressed radially inward.

The locking members can be tapered such that the outer diameter of the member at its proximal end is smaller than the outer diameter of the member at more distal locations. The largest outer diameter of the locking members is small enough to allow the locking members to pass through the tether lumen in the systems described herein that used stop members to secure the tether.

Figure 17:
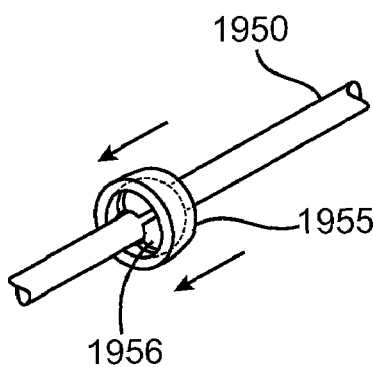

FIG. 17 shows another embodiment of a locking device having a shorter stop member 1955 and locking member 1956 on a tether 1950 than the stop member and locking member depicted in FIGS. 16A and 16B. In one embodiment of the invention, if a clinician determines that too much of the tension member has been withdrawn through the proximal helical anchor, a delivery sheath or similar device can be passed over the locking members to compress the legs inward. The sheath is then moved distally through the tether stop until the locking members are distal of the tether stop, at which time the sheath is withdrawn.

Other embodiments of stop members can have two biaxial lumens and the portion of the tether that is disposed in the inner channel of an annuloplasty device can have locking members at each end thereof, whereby the locking members at one end of the annuloplasty device are oriented in an opposite direction from the locking members at the other end of the annuloplasty device. In the embodiments having two lumens, the first and second ends of the tether are each passed through a different lumen and a force is applied to move the locking members through the lumens until the desired state of modification has been achieved.

In yet other embodiments having a single helical anchor, the tether can be secured to the helical anchor at one or both ends by stop members, and the tether can also be knotted to the stop members at one or both ends. Another method for securing the tether to a single helical anchor is to tie the tether to at least one end of the helical anchor.

Figure 18:
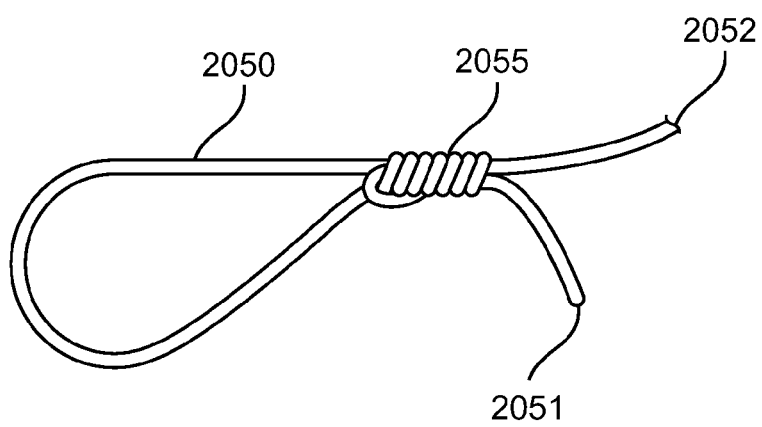
FIG. 18 illustrates an embodiment of a knot used as a locking devices used for annuloplasty devices according to the current invention.
Figure 20A:
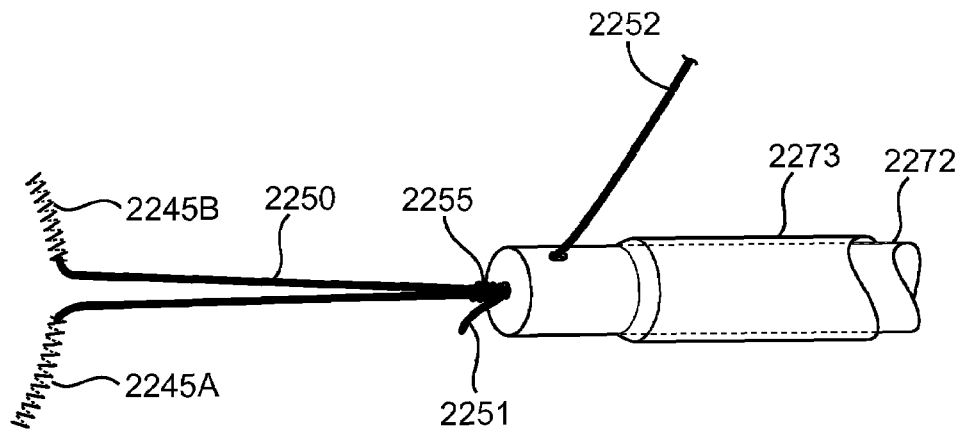
FIGS. 20A-20E illustrate a lock pusher-tether cutter device as it is used according to the current invention.
Figure 20B:
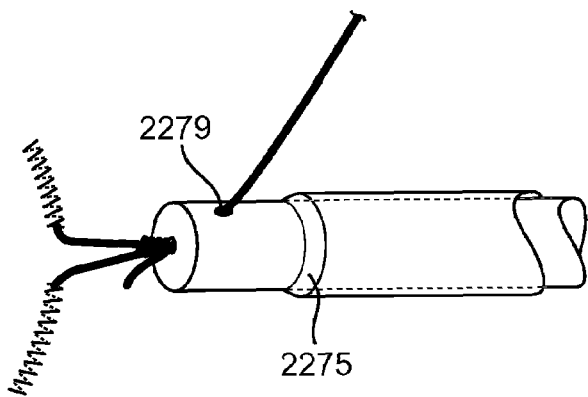
Figure 20C:
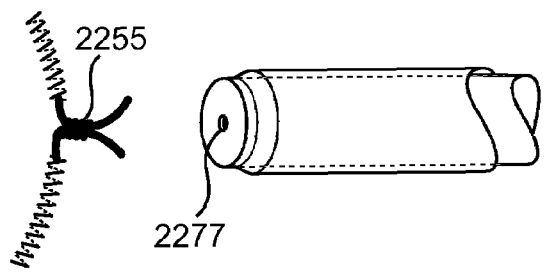
Figure 20D:
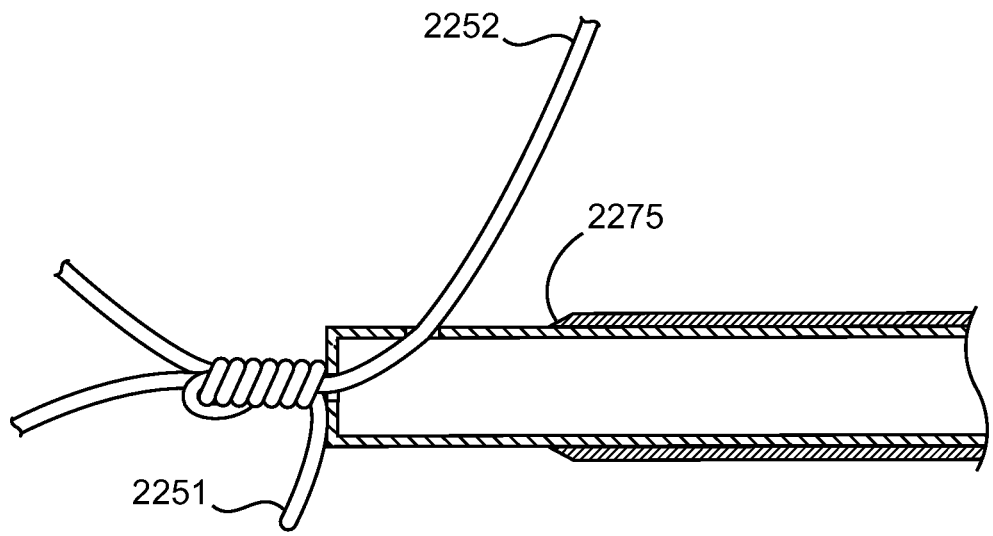
Figure 20E:
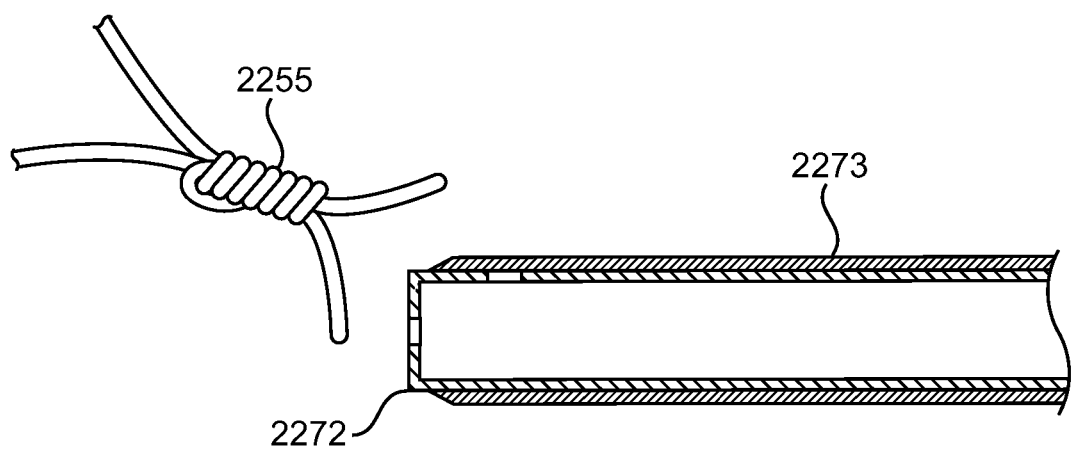

In some embodiments of the invention the locking device is a knot or friction hitch that is tied such that it can move in one direction along the tether but not in another direction. One skilled in the art of knot tying will recognize that there are several such knots or hitches that would be suited for use as a locking device. Regardless of the knot/hitch used, the locking device must only be able to move distally along the tether, and it must not slip after a loop has been tightened to modify the shape of a valve annulus. Referring now to FIG. 18 there can be seen another locking device according to the current invention, wherein the locking device is a knot. The knot 2055 shown in the figure is a snell or snelled knot wherein one end 2051 of the tether 2050 is tied to the other end of the tether 2052 to form a loop. The knot 2055 is then moved distally along the other end 2052 of the tether toward a helical anchor to make the loop smaller until the desired state of modification in the valve annulus has been achieved.

The locking devices of the current invention can be made from any suitable biocompatible material including polymeric material such as, but not limited to, polyurethane, polyethylene, nylon and polytetrafluoroethylene (PTFE). The locking devices can be made from can be made from rigid plastics or metals such as stainless steel or other suitable metals, and it can be made from a combination of two or more of these materials. One embodiment of the current invention has tether stops and locking devices made from stainless steel and another embodiment has tether stops made from hard plastic and locking devices made from a shape memory alloy. Still another embodiment of the invention has tether stops made from stainless steel and locking members made from a flexible biocompatible polymer.

Regardless of the locking device used to secure the tether and maintain the desired level of modification of the valve annulus, the locking device will likely be placed on the tether at a location outside of a patient's body and then moved distally along the tether. Additionally, once the valve annulus has been modified and the locking device has been secured, any excess tether must be removed from the patient's body.

Figure 19A:
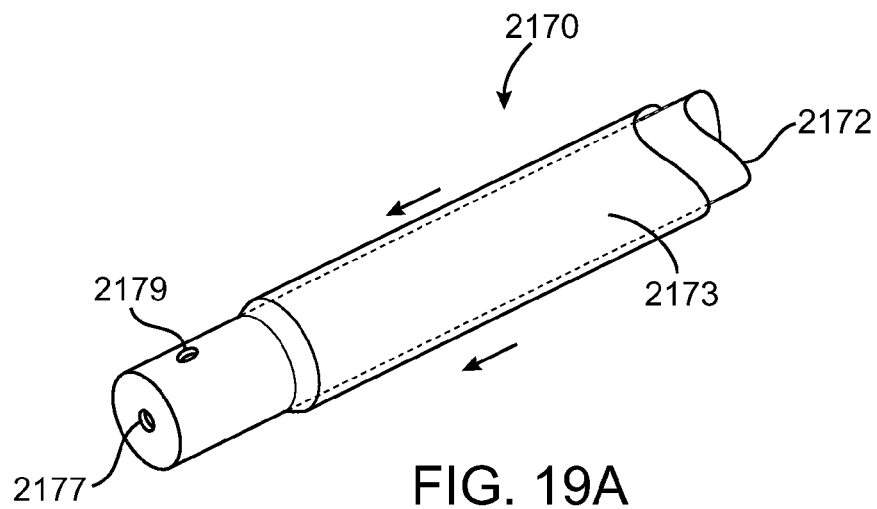
FIGS. 19A and 19B illustrates a lock pusher-tether cutter device according to the current invention.
Figure 19B:
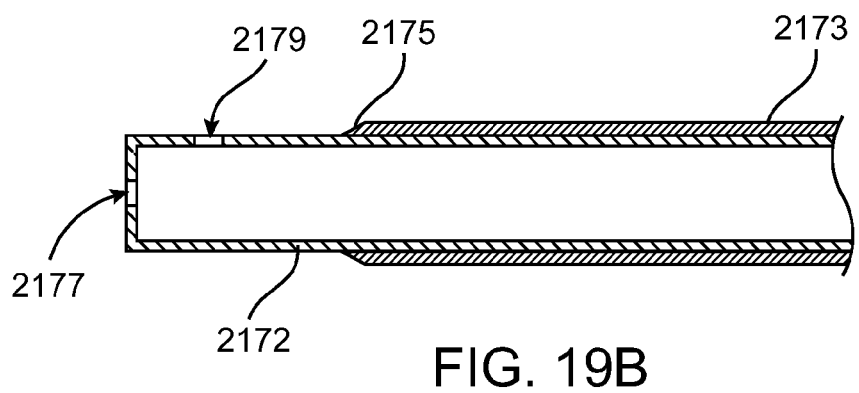

Referring now to FIGS. 19A and 19B, there is shown a lock pusher and tether cutting device 2170 according to the current invention. The lock pusher comprises a generally elongated tubular member 2172 having a distal end, a proximal end, a tether channel, an exterior, and an opening 2177 in the distal tip of the elongated member. At least one tether portal 2179 communicates from the exterior of the lock pusher into the tether channel on the distal portion of the lock pusher. The lock pusher is slidably disposed inside of a generally elongated tubular cutting member 2173 that has a sharpened blade portion 2175 located at a distal end thereof, and a proximal end.

Referring to FIGS. 20A through 20E; when the helical anchors 2245A and 2245B of an annuloplasty device according to the current invention is implanted in a heart valve annulus via minimally invasive surgery, the locking device 2255 will be placed on either the first end of the tether, the second end of the tether or both. As shown in the FIGS, the locking device is a knot 2255 made by tying the first end 2251 of the tether 2250 around a portion of the second end 2252 of the tether. The locking device will then be moved for a short distance in a distal direction so that the free end or free ends of the tether can be inserted into the opening 2277 in the distal tip of the lock pusher 2272 and then extend out of the tether portal 2279. The lock pusher will then be advanced to the helical anchor following the same path that the annuloplasty device delivery member followed. As the lock pusher is advanced distally from the ends of the tether a force is exerted on the helical anchor or helical anchors and the shape of the valve is modified.

Once a desired level of modification is achieved, the clinician stops the distal movement of the lock pusher and secures the free ends of the tether to prevent them from moving distally. Once the free ends of the tether are secured, the cutting member 2273 is slid towards the helical anchors along the exterior of the lock pusher while the lock pusher is held in place. The sharpened blade portion 2275 on the distal end of the cutting member cuts the tether so that any excess tether can be removed from a patient's body. The lock pusher is then withdrawn from the patient's body.

The distance between the distal end of the lock pusher and the tether portal is sufficient to prevent a locking member that is just proximal of a tether stop, from exiting the tether portal and being cut from the tether. If a friction hitch or other knot is used or if one end of the tether is secured to a tether stop via a knot, only one end of the tether will be free. Other embodiments of lock pushers according to the current invention can have the cutting member slidably disposed within the interior of the generally elongate tubular lock pusher.

If a tether stop having two biaxial lumens is used for a tether having locking members at both ends of the portion that is disposed within the inner channel of a helical anchor or helical anchors, one end of the tether is placed in the lock pusher while the other end is held outside of the patient's body. The lock pusher is then used to advance the tether stop distally to the helical anchor until the tether stop passes over one locking member. The lock pusher is then withdrawn and the other end of the tether is placed in the distal end of the lock pusher and out through the tether portal. The lock pusher is then advanced distally to engage the tether stop and advance the tether stop over the locking members on the tether until a desired degree of modification has been achieved for the valve annulus. The tether is then trimmed as described above and the lock pusher is withdrawn and used to trim the excess off of the other end of the tether as described above.

The components of the knot pusher and cutting member can be made from any suitable biocompatible material. The knot pusher can be made of flexible, biocompatible polymeric material such as, but not limited to, polyurethane, polyethylene, nylon and polytetrafluoroethylene (PTFE), it can be made from rigid plastics or metals such as stainless steel or other suitable metals, and it can be made from a combination of two or more of these materials.

The cutting member can also be made from flexible, biocompatible polymeric material such as, but not limited to, polyurethane, polyethylene, nylon and polytetrafluoroethylene (PTFE). Portions of the cutting member can be made from rigid plastics or metals such as stainless steel of other suitable metals as long as the distal portion of the driver is made from a flexible material that will allow it to negotiated curved portions of the delivery member. In one embodiment, the proximal portion of the cutting member is made from a flexible polymer and the sharpened blade portion is made from stainless steel and affixed to the distal end of the cutting member by a biocompatible adhesive.

The lumens of the lock pushers and cutting members of the current invention can be coated with a lubricious material such as silicone, polytetrafluroethylene (PTFE), or a hydrophilic coating. The lubricious interior surfaces facilitate the longitudinal movement the members relative to each other when the tether is being trimmed.

After the procedure is complete, the location of the locking device will be based on the number of helical anchors, the method used to deploy the helical anchors and the desire of the clinician. When the annuloplasty devices of the current invention are used to treat mitral regurgitation, it is possible to place the helical anchor device at any desire location along the valve annulus that does not have a helical anchor implanted in it. The most common locations for leaving the helical anchor when treating mitral regurgitation are along the annulus at a location adjacent the posterior commisure, at a location adjacent near the left trigone, at a point that is located along the anterior portion of the annulus, at a location near the right trigone, and at a location adjacent to the anterior commisure. Locking devices are generally located adjacent the posterior commisure or left trigone when the annuloplasty devices of the current invention have been implanted using a minimally invasive surgical procedure.

If the annuloplasty device uses a single helical anchor or if the clinician chooses to put a helical anchor stop or knot at each end of the device, as opposed to forming a loop, then the force is applied to reshape the annulus based on the method of access to the mitral valve. Access via a minimally invasive surgical procedure usually means that the shape modification force is applied from the proximal commisure or left trigone area.

When a clinician is manipulating the tether of the current invention to modify the valve annulus of a beating heart, such as with a minimally invasive surgical procedure, the degree of modification can be monitored using fluoroscopy or any other imaging procedure that is known for measuring valvular regurgitation. Once the desired degree of modification has been achieved, the tether is secured using a locking device as described above.

To achieve the desired degree of modification, a treating clinician must take care to not exert too much force on the valve annulus. Thus, the clinician should apply a force slowly and increase it incrementally while continuously monitoring. A clinician can also use a device for measuring the amount of force applied to ensure that not too much force is being used. This assists the clinician in making sure that the helical anchor is not pulled out of the valve annulus by too much force. In an embodiment having a single helical anchor implanted on the posterior portion of a mitral valve annulus between the posterior commisure and the anterior commisure and a single helical anchor along the anterior portion of the mitral valve annulus between the left and right trigone, maximum modification can be achieved by applying a constant tension force of six pounds close a loop and leave the helical anchor at a location adjacent to either the posterior commisure or the anterior commisure while constantly monitoring to check on the level of mitral regurgitation. In a single helical anchor embodiment or a multiple helical anchor embodiment implanted along the posterior commisure, and not using a loop, maximum modification can be achieved by applying constant tension force of just over four pounds from either end of the helical anchor or helical anchors. Once the desired state of modification has been achieved, and the tether lock has been placed, the annuloplasty device remains under a force load.

Figure 21:
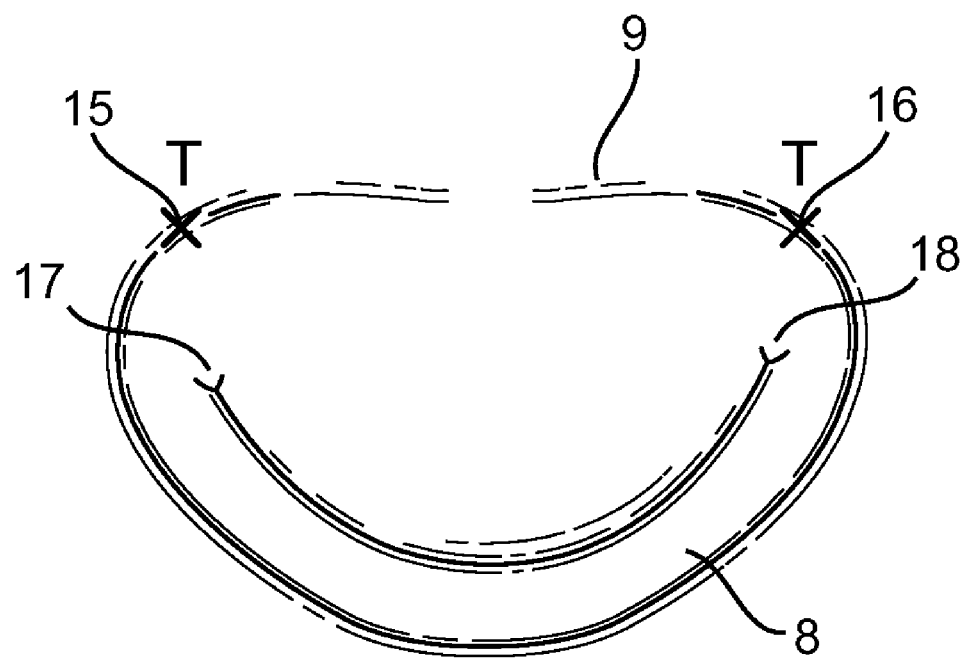
FIG. 21 illustrates the anatomy of a mitral valve.

FIG. 21 illustrates a mitral valve with the rest of the heart structure removed for clarity. The valve has a posterior commisure 17, an anterior commisure 18, an annulus with a posterior portion 8 and an anterior portion 9. A left trigone 15 and a right trigone 16 are located along the anterior portion of the annulus.

FIGS. 22-26 illustrate a variety of embodiments of annuloplasty devices according to the current invention. Delivery devices and their use for implanting the helical anchors has been described above, and as can be seen in FIGS. 22-26, the helical anchors of the current invention are implanted such that the inner channel of the anchors is generally parallel with the valve annulus. The devices shown in the FIGS. can be implanted in a temporarily stopped heart or in a beating heart using minimally invasive surgical methods to access the valve. To provide for clarity in the illustrations, the tethers are not shown in the inner channels of the helical anchors of the FIGS.

Figure 22:
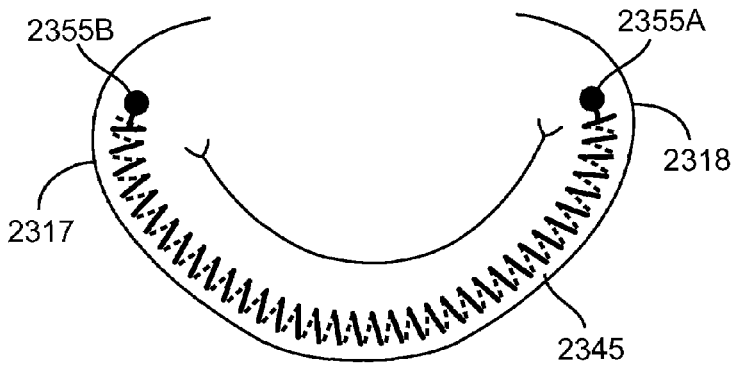
FIGS. 22-26 illustrate the placement of helical anchors and locking devices according to the current invention.

FIG. 22 illustrates a mitral valve having a single helical anchor 2345 implanted along the posterior portion of the annulus between the posterior commisure 2317 and the anterior commisure 2318. A tether (not shown) is disposed in the inner channel of the helical anchor and a pair of helical anchor stops 2355A and 2355B are disposed at the ends of the tether. The shape of the valve is modified by applying tension from either end of the helical anchor to shorten the length of the helical anchor along the annulus. In other embodiments of the invention having a single helical anchor, the tether can be tied to the helical anchor at one or both ends to secure the tether and to maintain the desired level of modification of the valve. Implanting a single helical anchor embodiment or a multiple helical anchor embodiment on the posterior side of a mitral valve annulus allows a clinician to avoid the portion of the valve near the aorta and thus reduces the potential for piercing the aorta wall.

Figure 23:
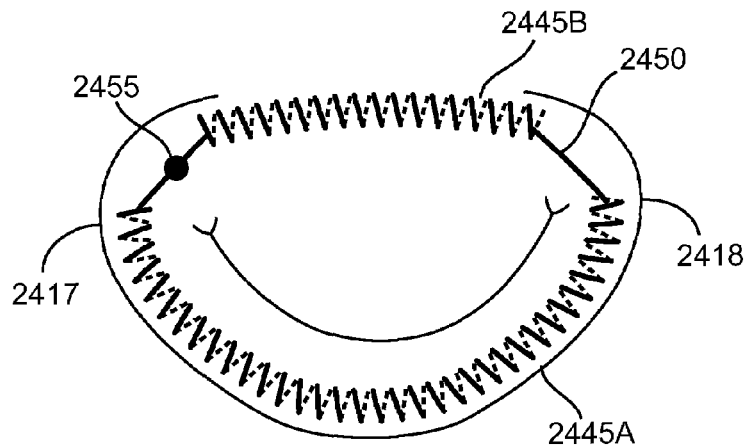

FIG. 23 illustrates an annuloplasty device according to the current invention having a single helical anchor 2445A implanted along the posterior portion of a mitral valve annulus between the posterior commisure 2417 and the anterior commisure 2418. Another helical anchor 2445B is implanted along the anterior portion of the valve annulus between the left and right trigones. A tether 2450 is disposed in the inner channels of the helical anchors and a tether lock 2455 is located at a point along the helical anchor that is adjacent to the posterior commisure. In this embodiment, the shape of the valve is modified by applying a force to make the loop in the tether smaller until the desired level of modification has been achieved and a locking device is placed on the tether to maintain the desired state of modification.

Figure 24:
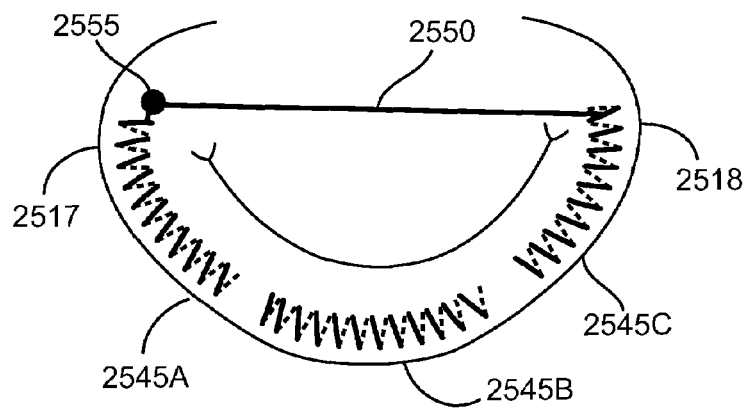

FIG. 24 illustrates a mitral valve having three helical anchors 2545A, 2545B, and 2545C implanted along the posterior portion of the annulus between the posterior commisure 2517 and the anterior commisure 2518. A tether 2550 is disposed in the inner channels of the helical anchors and a locking device 2555 is located adjacent to the posterior commisure. In this embodiment, the shape of the valve is modified by applying a force to make the loop in the tether smaller until the desired level of modification has been achieved and a locking device is placed on the tether to maintain the desired state of modification. In other embodiments having multiple helical anchors along the posterior portion of the annulus, a clinician may choose not to form a loop from the tether and the shape of the valve is modified by applying tension from either end of the group of helical anchors to shorten the length of the helical anchors along the annulus.

Figure 25:
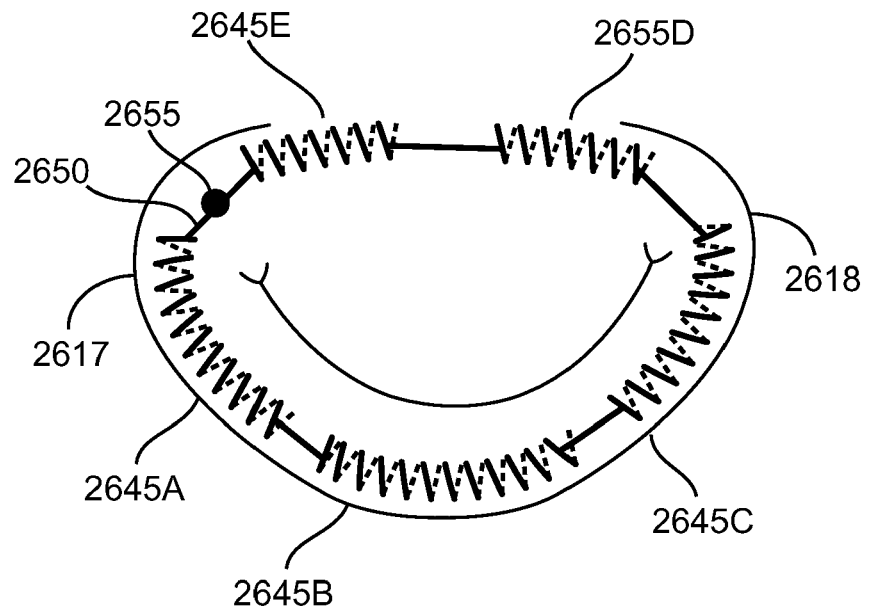

FIG. 25 illustrates a mitral valve having three helical anchors 2645A, 2645B, and 2645C implanted along the posterior portion of the annulus between the posterior commisure 2617 and the anterior commisure 2618. and a pair of helical anchors 2645D and 2645E along the anterior portion of the valve annulus between the left and right trigones. A tether 2650 is disposed in the inner channels of the helical anchors and a tether lock 2655 is located at a point along the helical anchor that is adjacent to the anterior commisure. In this embodiment, the shape of the valve is modified by applying a force to make the loop in the tether smaller until the desired level of modification has been achieved and a locking device is placed on the tether to maintain the desired state of modification.

Figure 26:
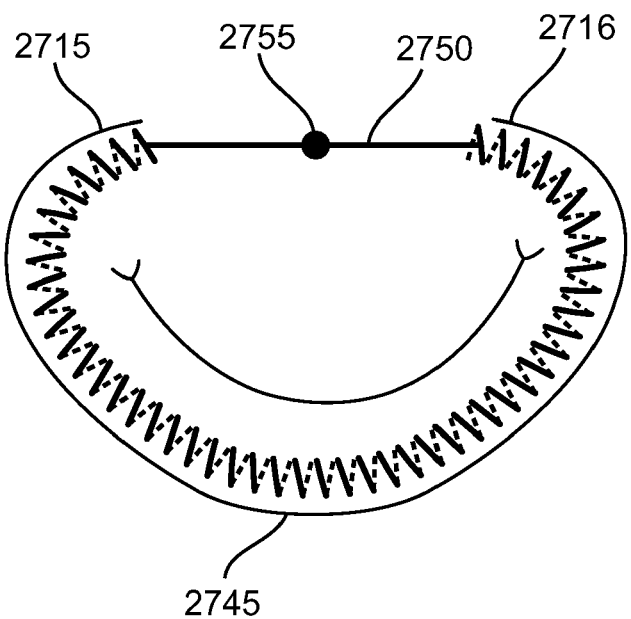

FIG. 26 illustrates a mitral valve having a single helical anchor 2745 implanted along the posterior portion of the annulus between left trigone 2715 and the right trigone 2716. A tether 2750 is disposed in the inner channels of the helical anchors and a locking device 2755 is located along the anterior portion of the annulus. In this embodiment, the shape of the valve is modified by applying a force to make the loop in the tether smaller until the desired level of modification has been achieved and a locking device is placed on the tether to maintain the desired state of modification. In other embodiments having a single helical anchor, a clinician may choose not to form a loop from the tether and the shape of the valve is modified by applying tension from either end of the helical anchor to shorten the length of the helical anchor along the annulus.

The helical anchors of the annuloplasty devices shown and discussed above are longitudinally implanted in an annulus of a heart valve. In embodiments using a single helical anchor, the number of coils per inch and the thickness of the material used for the helical anchors are selected to allow the helical anchors to be longitudinally contracted after they are implanted.

After the helical anchors are implanted in the annulus of a heart valve (as described above), a force is applied to the tether. The force on the tether modifies the shape of the valve annulus and increases coaption of the valve leaflets.

The helical anchors can be longitudinally implanted into a valve annulus via minimally invasive surgical delivery as described above One exemplary method that can be used for accessing a beating heart via minimally invasive surgical procedures to treat mitral regurgitation generally can start with intubating a patient with a double-lumen endobronchial tube that allows selective ventilation or deflation of the right and left lungs. The left lung is deflated, thereby helping to provide access to the surface of the heart. The patient is rotated approximately 30 degrees with the left side facing upwardly. The left arm is placed below and behind the patient so as not to interfere with tool manipulation during the procedure. While port positions depend to a large extent on heart size and position, in general a seventh and fifth space mid (to posterior) axillary port for tools and a third space anterior axillary port for the scope is preferable. A variety of endoscopes or thoracoscopes may be used including a 30-degree offset viewing scope or a straight ahead viewing scope. In general, short 10 to 12 mm ports are sufficient. Alternatively, a soft 20 mm port with an oval cross-section sometimes allows for two tools in the port without compromising patient morbidity.

Figure 27:
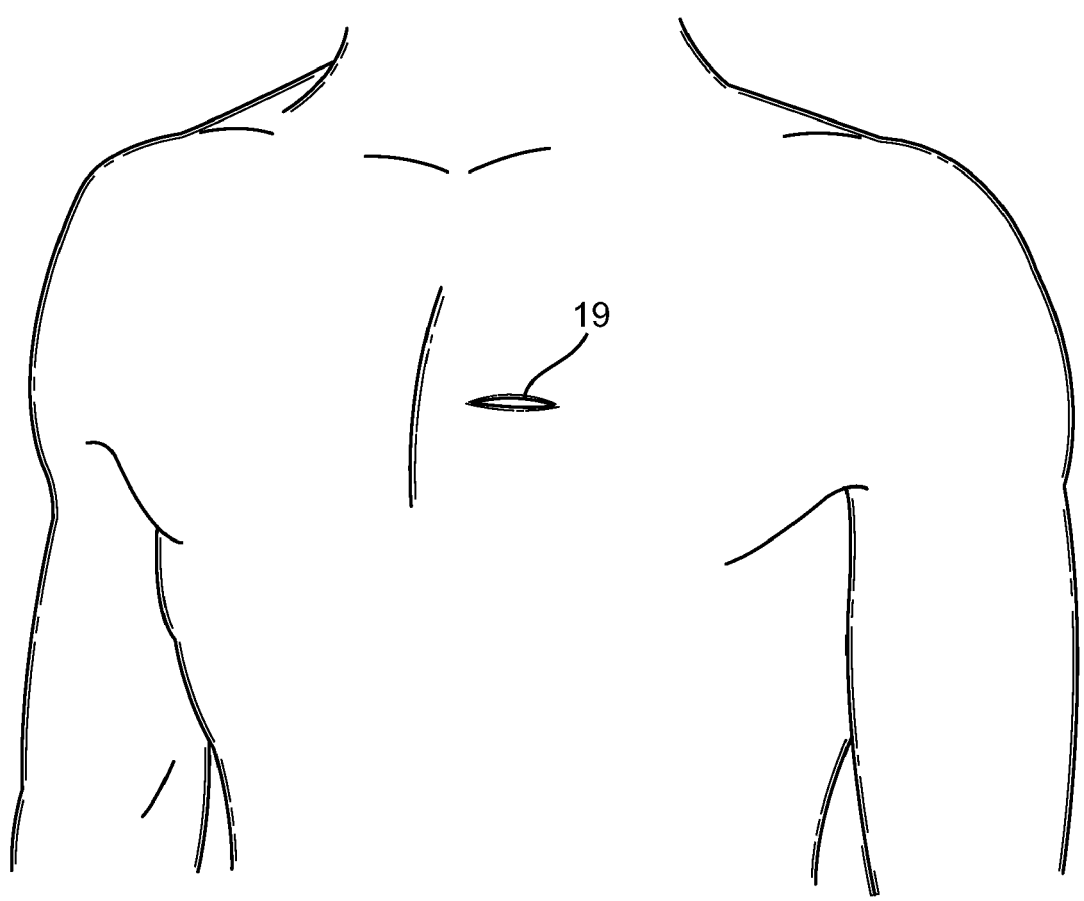
FIGS. 27-31 illustrate a minimally invasive surgical method for implanting helical anchored annuloplasty devices to treat mitral regurgitation according to the current invention.

In one embodiment of the present invention, passages are made through a patient's skin into the thoracic cavity, such as the passage 19 illustrated in FIG. 27. The passages may be formed by employing one-piece rods or trocars of prescribed diameters and lengths that are advanced through body tissue to form the passage, which are subsequently removed so that other instruments can be advanced through the passage. The passage may instead be formed by employing two-piece trocars that comprise a tubular outer sleeve, which is sometimes referred to as a port or cannula or as the tubular access sleeve itself, having a sleeve access lumen extending between lumen end openings at the sleeve proximal end and sleeve distal end. The two-piece trocar can further include an inner puncture core or rod that fits within the sleeve access lumen. The inner puncture rod typically has a tissue penetrating distal end that extends distally from the sleeve distal end when the inner puncture rod is fitted into the sleeve access lumen for use. The two-piece trocar can be assembled and advanced as a unit through body tissue, and then the inner puncture rod is removed, thereby leaving the tubular access sleeve in place to maintain a fixed diameter passage through the tissue for use by other instruments.

In one embodiment, a tubular access sleeve is placed through a passage that is made as described above in the chest wall of a patient between the patient's second rib and sixth rib, for example. The selection of the exact location of the passage is dependent upon a patient's particular anatomy. A further conventional tubular access sleeve can be placed in a different passage that is also made in the chest wall of patient.

In accordance with one method used in the invention, the patient's left lung is deflated to allow unobstructed observation of the pericardium employing a thoracoscope or other imaging device that is inserted through a sleeve lumen of a tubular access sleeve. The thoracoscope or other imaging device may have its own light source for illuminating the surgical field. Deflation of the patient's lung may be accomplished in a number of ways, such as by inserting a double lumen endotracheal tube into the trachea, and independently ventilating the right, left or both lungs. The left lung can be collapsed for visualization of the structures of the left hemisternum when ventilation of the left lung is halted and the left thoracic negative pressure is relieved through a lumen of the tubular access sleeve or a further access sleeve to atmospheric pressure. After deflation, the thoracic cavity may be suffused with a gas (e.g., carbon dioxide) that is introduced through a lumen of the tubular access sleeve or the further access sleeve to pressurize the cavity to keep it open and sterile. The pressurized gas keeps the deflated lung away from the left heart so that the left heart can be viewed and accessed and provides a working space for the manipulation of the tools of the present invention. It will be understood that the access sleeve lumens must be sealed with seals about instruments introduced through the lumens if pressurization is to be maintained.

A thoracoscope can then be inserted into the lumen of a tubular access sleeve to permit wide angle observation of the thoracic cavity by a surgeon directly through an eyepiece or indirectly through incorporation of a miniaturized image capture device (e.g., a digital camera) at the distal end of the thoracoscope or optically coupled to the eyepiece that is in turn coupled to an external video monitor. The thoracoscope may also incorporate a light source for illuminating the cavity with visible light so that the epicardial surface can be visualized. The thoracoscope may be used to directly visualize the thoracic cavity and obtain a left lateral view of the pericardial sac or pericardium over the heart.

The elongated access sleeve provides an access sleeve lumen, enabling introduction of the distal end of a pericardial access tool. The tubular access sleeve and the pericardial access tool are employed to create an incision in the pericardial sac so that the clinician can view and access the left free wall of the heart. After the clinician gains access to the heart, a continuous circular suture (commonly know and referred to herein as a purse string suture) is placed in the free wall of the left atrium at a location near the commisure of the mitral valve, and above the coronary sinus. The wall is then punctured inside the perimeter of the suture. The wall can be punctured using a special puncture device, or the distal end of the delivery members described herein can be used to puncture the wall.

The distal end of a first delivery member can then be advanced through the elongated access sleeve, through the puncture formed through the myocardium, and placed against the mitral valve annulus on either the anterior leaflet side (anterior side) or posterior leaflet side (posterior side) of the valve. At least a portion of a device for treating mitral regurgitation can then be implanted. The first delivery member is then withdrawn. The distal end of a second delivery member, which may be generally the same or different from the delivery member 10, is then advanced through the elongated access sleeve, through the puncture formed through the myocardium, and placed against the mitral valve annulus on the other of the anterior or posterior side of the valve. The remainder of the device for treating mitral regurgitation can then be implanted. The second delivery member is then withdrawn and the purse string is tightened to close the puncture. The lung can then be inflated, the instruments withdrawn from the patient, and all openings closed. The procedure outside of the heart can be viewed through a scope as disclosed above, and the procedure inside the heart can be visualized and imaged using fluoroscopy, echocardiography, ultrasound, EM imaging, other suitable means of visualization/imaging, or combinations of the aforementioned visualization methods. Visualization techniques may also be used to map the heart prior to beginning the minimally invasive procedure. Mapping the heart provides details as to the size and shape of the valve annulus to be treated and the extent of deformation of the valve, itself.

Figure 28:
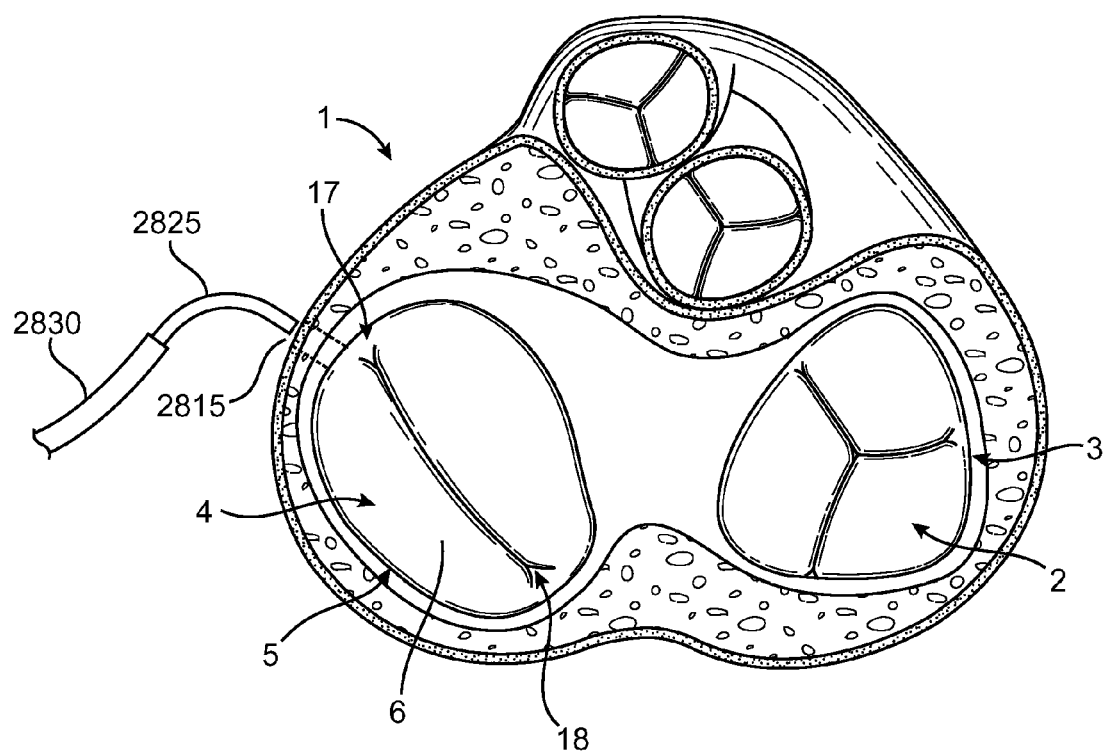
Figure 29:
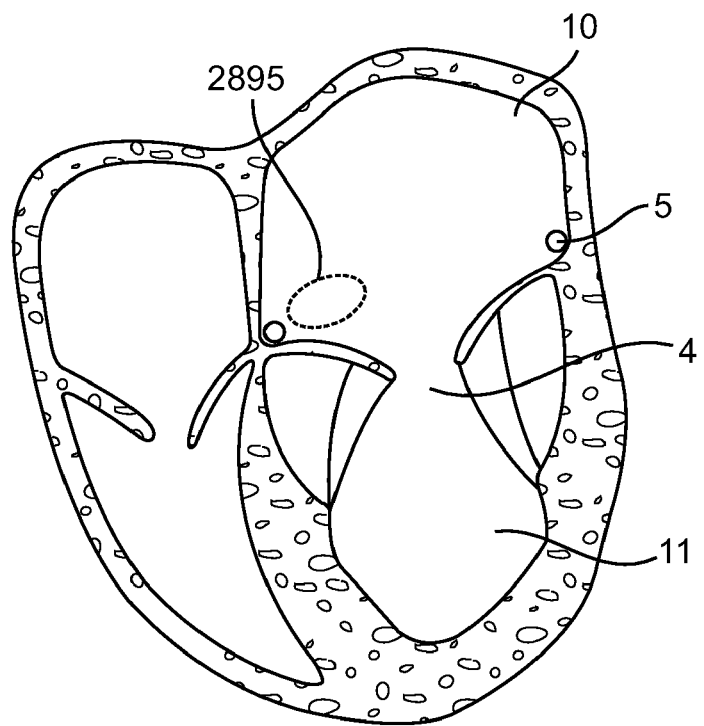
Figure 30:
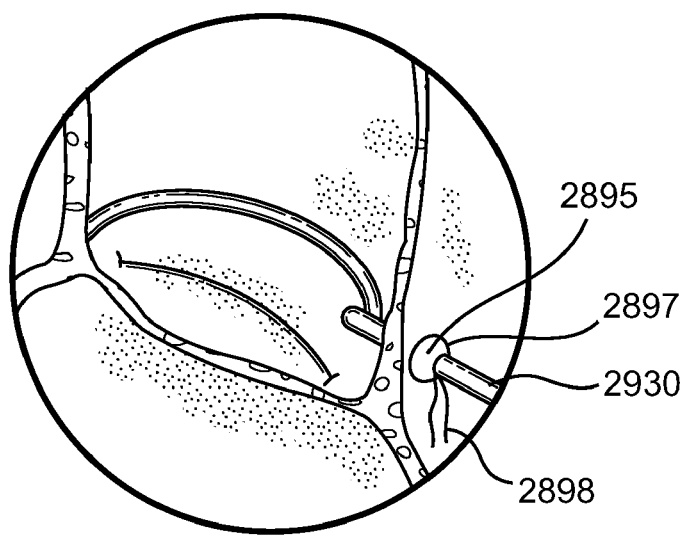

FIGS. 28, 29, and 30 illustrate an exemplary placement of delivery members of the current invention inside the heart. FIGS. 28 and 29 are illustrations showing cross-sectional views of a heart 1 having tricuspid valve 2 and tricuspid valve annulus 3. Mitral valve 4 is adjacent mitral valve annulus 5. Mitral valve 4 is a bicuspid valve that regulates blood flow between the left atrium 10 and the left ventricle 11 the valve further having anterior cusp 7 and posterior cusp 6. Anterior cusp 7 and posterior cusp 6 are often referred to, respectively, as the anterior and posterior leaflets. Also shown in the figure are the posterior commisure 17 and the anterior commisure 18. A purse string suture has been placed in the heart and the wall 2815 is punctured (as described above) at a location 2895 (shown in FIG. 29) in the atrium wall that is adjacent the posterior commisure of the posterior and anterior cusp and above the coronary sinus. An elongated, generally tubular annuloplasty device delivery member 2830 having an anchor guide 2825 can then be placed into the heart and positioned on the valve annulus for implantation of an annuloplasty device having a single helical anchor or a plurality of helical anchors.

Referring particularly to FIG. 30, the location of the puncture site 2895 is visible inside of the purse string suture 2897 (the free ends 2898 of the which are visible in the figure), and a portion of a delivery member 2930 is illustrated for delivering an annuloplasty device the posterior portion of a mitral valve annulus. A helical anchor can thereby be implanted in the correct location.

Figure 31:
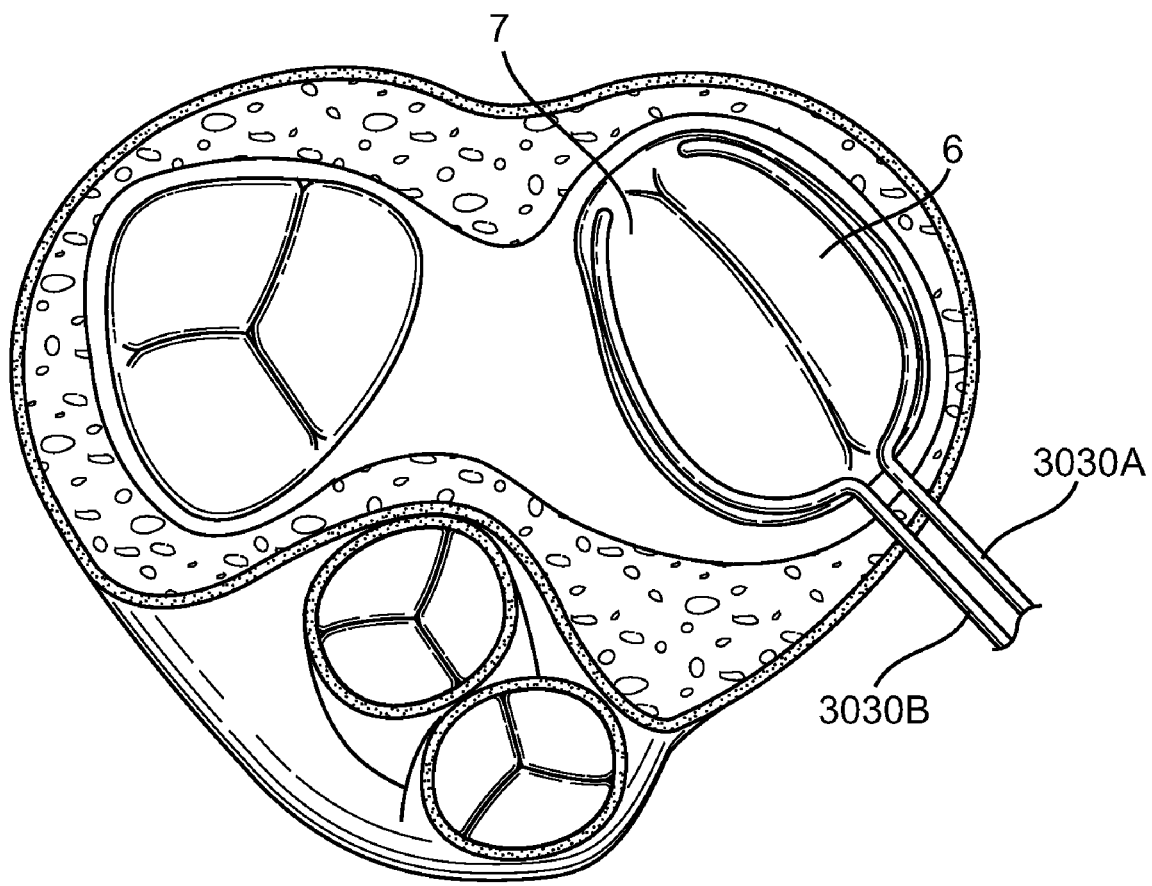

Referring now to FIG. 31, a schematic cross-section of a heart is illustrated showing two delivery members 3030A and 3030B on a mitral valve annulus adjacent to anterior cusp 7 and posterior cusp 6. In practice, the delivery members are not inside of the heart at the same time, the figure shows how the posterior delivery member 3030A and the anterior delivery member 3030B are shaped to provide for insertion of helical anchors along a major portion of a valve annulus. The distal portions of the delivery members can be sized and shaped for a particular annulus based on the previously performed imaging and mapping. As is represented by the exemplary pronounced curvature of the distal section of the posterior delivery member in this figure, the distal section is relatively rigid so that the heart walls can be shaped to conform to the shape of the valve annulus and the device distal section for implantation of the helical anchor of a helically helical anchored device or ring.

Figure 32:
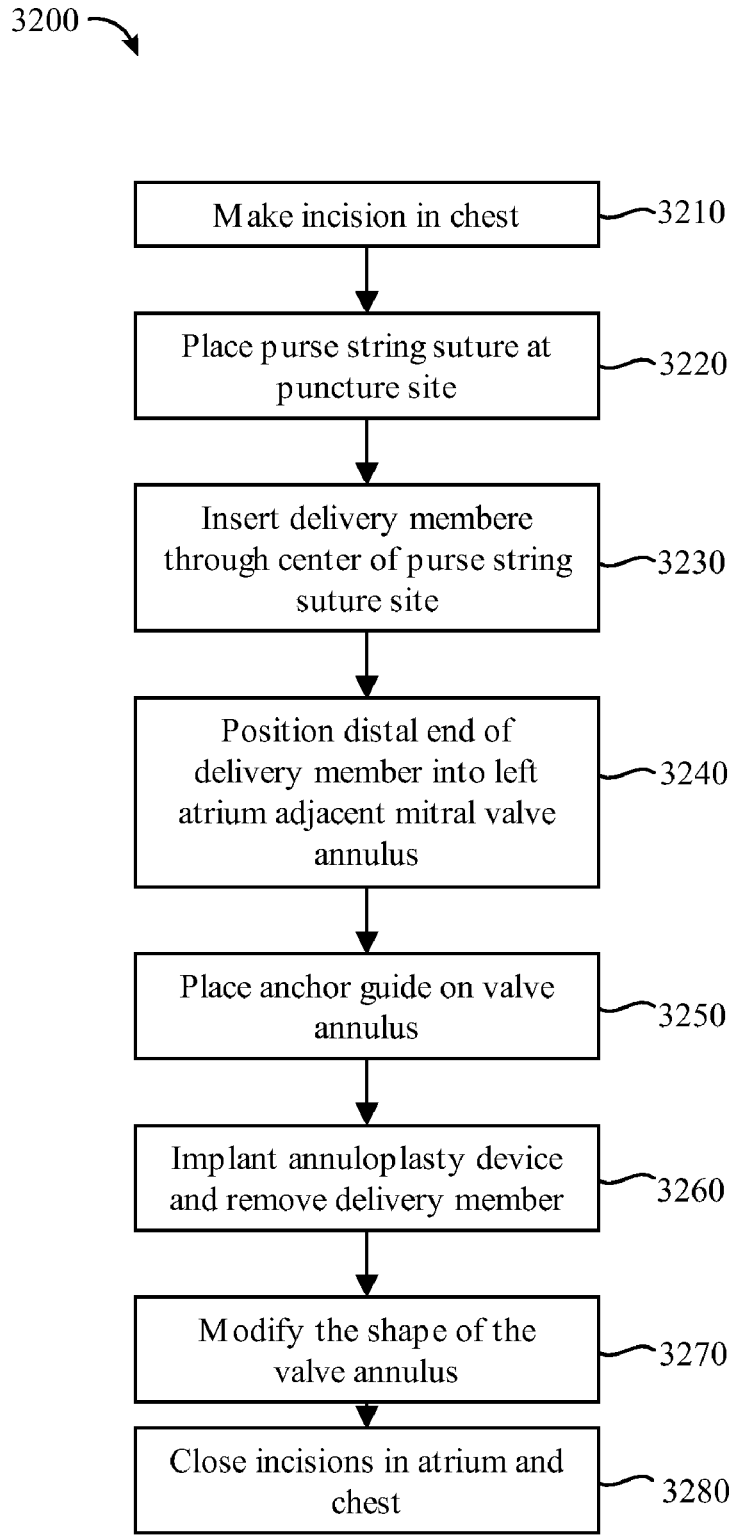
FIG. 32 is a flow chart of one embodiment of a method for implanting a helically helical anchored annuloplasty device according to the current invention.

FIG. 32 is a block diagram showing a method 3200 for implanting helically anchored annuloplasty rings according to the current invention. One embodiment of the current method begins by making an incision in a patient's chest 3210 and placing a purse string suture at a puncture site in the wall of the patient's heart 3220. Next, the heart wall is punctured and a delivery member is inserted through center of purse string suture site 3230. The distal end of the delivery member is positioned in the left atrium adjacent mitral valve annulus 3240 and the anchor guide is place on the valve annulus 3250. A helically anchored annuloplasty device is then implanted into the valve annulus 3260 and the shape of the annulus is modified 3270. The tether is then secured and the incisions are closed 3280 to complete the procedure.

While the invention has been described with reference to particular embodiments, it will be understood by one skilled in the art that variations and modifications may be made in form and detail without departing from the spirit and scope of the invention.

What is claimed is:

1. A method for modifying a heart valve annulus, comprising:

accessing a heart via a passage made through a patient's skin into the thoracic cavity;

placing a continuous circular suture around a puncture site in the wall of the patient's heart adjacent a heart valve;

puncturing the heart at the puncture site;

inserting a distal end of at least one elongated delivery member for an annuloplasty device through the puncture site;

positioning the distal end of the at least one delivery member adjacent a portion of a valve annulus;

deploying an annuloplasty device comprising at least one helical anchor and an elongated flexible tether, the helical anchor having a long axis, a distal end with a sharpened tip portion, a proximal end, and a plurality of coils defining an inner channel that communicates along the length of the helical anchor and the tether having a first end and a second end;

implanting the annuloplasty device by rotating the helical anchor into the valve annulus such that the long axis of the helical anchor extends along the valve annulus such that the anchor and inner channel are generally parallel with the valve annulus, and the tether is routed through the inner channel such that one end of the tether extends from the distal end of the helical anchor and the other end of the tether extends from the proximal end of the helical anchor;

creating a loop in the tether by securing the first end of the tether to the second end of the tether with a locking device that can be moved along the tether away from the second end when a force is applied to move the locking device away from the second end but cannot be moved back toward the second end of the tether if the loop is tightened to the point that it is subjected to tension;

making the loop smaller by moving the locking device away from the second end of the tether until the locking device passes through the puncture site and the shape of the heart valve annulus begins to be modified;

monitoring the modification of the shape of the heart valve annulus while continuing to make the loop smaller until a desired level of modification is reached;

inserting a cutting device into the puncture site;

cutting the tether at a location that is adjacent the locking device but between the locking device and the second end of the tether;

withdrawing the cutting device from the puncture site;

withdrawing the delivery member from the puncture site; and tightening the suture to close the puncture site;

wherein the locking device is at least one stop member that has a size and shape such that it cannot pass through the inner channel of the at least one helical anchor;

the at least one stop member having at least one tether channel passing therethrough, and the tether further comprising a plurality of locking members spaced along at least a portion of the tether adjacent the first end of the tether; and wherein the locking members are configured to allow them to pass through the tether channel in one direction and not pass through the tether channel in the opposite direction.

2. The method of claim 1 wherein the at least one stop member having at least one tether channel is a single stop member having two tether channels; and wherein the first end of the tether is secured in one of the tether channels and the second end of the tether can be slidably inserted in the other tether channel.

3. The method of claim 1 wherein multiple elongated delivery members are used, and the annuloplasty device comprises a plurality of helical anchors and one elongated flexible tether.

4. The method of claim 3 comprising the additional steps of:

inserting a distal end of an additional elongated delivery member through the puncture site;

positioning the distal end of the additional delivery member adjacent a portion of a valve annulus;

deploying an additional helical anchor having a long axis, a distal end with a sharpened tip portion, a proximal end, a plurality of coils defining an inner channel that communicates along the length of the additional helical anchor;

implanting the additional helical anchor by rotating the additional helical anchor into the valve annulus such the long axis of the additional helical anchor extends along the valve annulus and the tether is routed through the inner channel such that one end of the tether extends from the distal end of the additional helical anchor and the other end of the tether extends from the proximal end of the additional helical anchor;

withdrawing the additional delivery member from the puncture site; and repeating the steps of inserting and positioning the distal end of an additional delivery member, deploying and implanting an additional helical anchor, and withdrawing the additional delivery member until a predetermined number of helical anchors has been implanted.

5. The method of claim 4 wherein the number of helical anchors implanted is in the range of two to six.

* * * * *